US008361725B2

(12) United States Patent
Russell et al.

(10) Patent No.: US 8,361,725 B2
(45) Date of Patent: *Jan. 29, 2013

(54) DETECTION AND TYPING OF BACTERIAL STRAINS

(75) Inventors: W. Michael Russell, Newburgh, IN (US); Rodolphe Barrangou, Madison, WI (US); Philippe Horvath, Scorbé-Clairvaux (FR)

(73) Assignee: DuPont Nutrition Biosciences APS, Copenhagen K (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/037,926

(22) Filed: Mar. 1, 2011

(65) Prior Publication Data

US 2011/0300541 A1    Dec. 8, 2011

Related U.S. Application Data

(62) Division of application No. 11/115,873, filed on Apr. 27, 2005, now Pat. No. 7,919,277.

(60) Provisional application No. 60/566,007, filed on Apr. 28, 2004.

(51) Int. Cl.
*C12Q 1/68* (2006.01)
*C12P 19/34* (2006.01)

(52) U.S. Cl. ..................... 435/6.12; 435/6.1

(58) Field of Classification Search ............... None
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 5,412,087 A | 5/1995 | McGall |
| 5,545,531 A | 8/1996 | Rava et al. |
| 5,753,467 A | 5/1998 | Jensen et al. |
| 5,837,832 A | 11/1998 | Chee |
| 5,861,242 A | 1/1999 | Chee |
| 6,395,475 B1 | 5/2002 | Leggett et al. |
| 6,610,836 B1 | 8/2003 | Breton et al. |
| 6,632,633 B1 | 10/2003 | Slijkhuis et al. |
| 7,468,182 B2 | 12/2008 | Klaenhammer et al. |
| 2002/0034748 A1 | 3/2002 | Quake et al. |
| 2002/0055628 A1 | 5/2002 | Keim et al. |
| 2003/0219778 A1 | 11/2003 | Ferreira et al. |

FOREIGN PATENT DOCUMENTS

| WO | WO 9500530 | 1/1995 |
| WO | 03/849989 | 10/2003 |

OTHER PUBLICATIONS

Cowan, L.S., and Crawford, J.T., "Genotype Analysis of Mycobacterium tuberculosis Isolates from a Sentinael Surveillance Population," Emerging Infectious Diseases, Nov. 2002, pp. 1294-1302, vol. 8, No. 11.

Driscoll, J.R., et al., "Spoligologos: A Bioinformatic Approach to Displaying and Analyzing Mycobacterium tuberculosis Data," Emerging Infectious Diseases, Nov. 2002, pp. 1306-1309, vol. 8, No. 11.

Ertugrul, N., et al, "BOX-polymerase Chain Reaction-based DNA Analysis of Nonserotypeable *Streptococcus pneumoniae* Implicated in Outbreaks of Conjunctivitis," J. Infect. Dis., Nov. 1997, pp. 1401-1405, vol. 176, No. 5.

Filliol, I., et al., "Detection of a Previously Unamplified Spacer Within the DR Locus of Mycobacterium tuberculosis: Epidemiological Implications," J. Clin. Microbiol., Mar. 2000, pp. 1231-1234, vol. 38, No. 3.

Groenen, P.M., et al., "Nature of DNA Polymorphism in the Direct Repeat Cluster of Microbacterium tuberculosis; Application for Strain Differentiation by a Novel Typing Method," Mol. Microbiol., 1993, pp. 1057-1065, vol. 10.

Ishino, Y., et al., "Nucleotide Sequence of the iap Gene, Responsible for Alkaline Phosphatase Isozyme Conversion in *Escherichia coli*, and Identification of the Gene Product," J. Bacteriol., 1987, pp. 5429-5433, vol. 169.

Jansen, R., et al., "Identification of Genes that are Associated with DNA Repeats in Prokaryotes," Molecular Microbiology, 2002, pp. 1565-1576, vol. 43, No. 6.

Jansen, R., et al., "Identification of a Novel Family of Sequence Repeats Among Prokaryotes," OMICS, A Journal of Integrative Biology, 2002, pp. 23-33, vol. 6, No. 1.

Kamerbeek, J., et al., "Simultaneous Detection and Strain Differentiation of Mycobacterium tuberculosis for Diagnosis and Epidemiology," J. Clin. Microbiol., Apr. 1997, pp. 907-914, vol. 35, No. 4.

Kanduma, E., et al., "Molecular Methods for Mycobacterium tuberculosis Strain Typing: A Users Guide," Journal of Applied Microbiology, 2003, pp. 781-791, vol. 94.

Mojica, F.J., et al., "MicroCorrespondence: Biological Significance of a Family of Regularly Spaced Repeats in the Genomes of Archaea, Bacteria and Mitochondria," Molecular Microbiology, 2000, pp. 244-246, vol. 36, No. 1.

Mokrousov, I., et al., "Novel IS6110 Insertion Sites in the Direct Repeat Locus of Mycobacterium tuberculosis Clinical Strains from the St. Petersburg Area of Russia and Evolutionary and Epidemiological Considerations," J. Clin Microbiol., Apr. 2002, pp. 1504-1507, vol. 40, No. 4.

Van Belkum, A., et al., "Novel BOX Repeat PCR Assay for High-Resolution Typing of *Streptococcus pneumoniae* Strains," J. Clin. Microbiol., May 1996, pp. 1176-1179, vol. 34, No. 5.

Van Belkum, A., et al., "Short-Sequence DNA Repeats in Prokaryotic Genomes," Microbiol. Mol. Biol. Rev., Jun. 1998, pp. 275-293, vol. 62, No. 2.

Van Der Zanden, A.G.M., et al., "Improvement of Differentiation and Interpretability of Spoligotyping for Mycobacterium tuberculosis Complex Isolates by Introduction of New Spacer Oligonucleotides," J. Clin. Microbiol., Dec. 2002, pp. 4628-4639, vol. 40, No. 12.

(Continued)

*Primary Examiner* — Young J Kim
(74) *Attorney, Agent, or Firm* — Steptoe & Johnson LLP

(57) ABSTRACT

Methods for the detection and typing of bacterial strains from food products and dietary supplements, environmental samples, in vivo/in vitro samples, and for studying the natural diversity of the species are disclosed. Potential applications also include product development and/or detection and differentiation of new bacterial strains.

8 Claims, 7 Drawing Sheets

OTHER PUBLICATIONS

Altermann et al., "Complete genome sequence of the probiotic lactic acid bacterium *Lactobacillus acidophilus* NCFM." Proceedings of the National Academy of Sciences of USA, vol. 102, No. 11, p. 3906-3912 (2005).
Berthier et al., "Rapid species identification within two groups of closely related lactobacilli using PCR primers that target the 16S/23S rRNA spacer region." FEMS Microbiology Letters, Amsterdam, NL., vol. 161, No. 1, p. 97-106 (1998).
Database EMBL (Online), Accession No. AA934301, "SWOvL3CAN12H09 Onchocerca volvulus infective larva cDNA (SAW94WL-OvL3) Onchocerca volvulus cDNA clone onch669 5', mRNA sequence." (Apr. 29, 1998).
Database EMBL (Online), Accession No. AR383507, "Sequence 236 from US Patent 6610836." (Dec. 19, 2003).
Database EMBL (Online), Accession No. AR408683, "Sequence 43 from US Patent 6632633." (Dec. 19, 2003).
Database EMBL (Online), Accession No. AY341565, "*Lactobacillus brevis* strain BJ1-1 16S ribosomal RNA gene, partial sequence." (Aug. 28, 2003).
Database EMBL (Online), Accession No. AZ587570, "1M0395P16F Mouse 10kb plasmid UUGC1M library Mus musculus genomic clone UUGC1M0395P16 F, DNA sequence." (Dec. 17, 2000).
Database EMBL (Online), Accession No. CB550968, "MMSP0038.sub.—F12 MMSP Macaca mulatta cDNA, mRNA sequence." (Jun. 3, 2003).
Jansen Rund et al., "Identification of a novel family of sequence repeats among prokaryotes." OMICS A. Journal of Integrative Biology, vol. 6, No. 1, p. 23-33 (2002).
Kanduma et al., "Molecular Methods for Mycobacterium tuberculosis strain typing: A users guide." Journal of Applied Microbiology, vol. 94, No. 5, p. 781-791 (2003).
Song et al., "Rapid identification of 11 human intestinal Lactobacillus species by multiplex PCR assays using group- and species specific primers derived from the 16S-23S rRNA intergenic spacer region and its flanking 23S rRNA." FEMS Microbiology Letters, Amsterdam, NL., vol. 187, No. 2, p. 167-173 (2000).
Supply et al., "Variable human minisatellite-like regions in the Mycobacterium tuberculosis genome." Molecular Microbiology, vol. 36, No. 3, p. 762-771 (2000).
Altschul, S.F., et al., Basic Local Alignment Search Tool, J. Mol. Biol., 1990, 215:403-410.
Altschul, S.F., et al., Gapped BLAST and PSI-BLAST: a new generation of protein database search programs, Nucleic Acids Res. 1997, vol. 25, No. 17, p. 3389-3402.
Amann, R. I., et al., Fluorescent-Oligonucleotide Probing of Whole Cells for Determinative, Phylogenetic, and Environmental Studies in Microbiology, J. Bacteriology, 1990, vol. 172, No. 2, p. 762-770.
Ausubel, et al., eds.Current Protocols in Molecular Biology (John Wiley & Sons, New York (1989)), Hybridization With Radioactive Probes, Unit 6.3-6.4, pp. 190-191.
Ausubel, et al., eds. (1995) Short Protocols in Molecular Biology, Chapter 2 (Greene Publishing and Wiley-Interscience, New York); pp. 2-1-2-44.
Database EMBL accession No. EMI_PRO:AX926711 "Sequence from Patent WO03084989".
Dieffenbach and Dveksler (1995) PCR Primer, a Laboratory Manual (Cold Spring Harbor Press, Plainview, N.Y.
U.S. Appl. No. 60/622,712, filed Oct. 27, 2004, Todd R. Klaenhammer, et al.
Gait, ed. (1984) Oligonucleotide Synthesis a Practical Approach (IRL Press, Oxford, England.
Hoe, N., et al., Rapid Molecular Genetic Subtyping of Serotype M1 Group A *Streptococcus Strains*, Emerg. Infect. Dis., 1999, 5:254-263.
Innis, et al., eds. (1999) PCR Applications: Protocols for Functional Genomics (Academic Press, New York).
Innis, et al., eds. (1990) PCR Protocols: A Guide to Methods and Applications (Academic Press, New York).
Karlin, S. and Altschul, S.F., Methods for assessing the statistical significance of molecular sequence features by using general scoring schemes, Proc. Natl. Acad. Sci. USA, 1990, 87, p. 2264-2268.
Karlin, S. and Altschul, S.F., Applications and statistics for multiple high-scoring segments in molecular sequences, Proc. Natl. Acad. Sci. USA, 1993, vol. 90, No. 12, p. 5873-5877.
Kleerebezem, M., et al., Complete genome sequence of *Lactobacillus plantarum* WCFS1, Proc. Natl. Acad. Sci. U.S.A., 2003, vol. 100, No. 4, p. 1990-1995.
Marshall, D.G., et al., Genomic DNA fingerprinting of clinical isolates of *Helicobacter pylori* using short oligonucleotide probes containing repetitive sequences, J. Appl. Bacteria, 1996, vol. 81, No. 5, p. 509-517.
Masepohl, B., et al., Long tandemly repeated repetitce (LTRR) sequences in the filamentous cyanobacterium Anabaena sp. PCC 7120 Biochimica Biophysica Acta, 1996, 1307:26-30.
Meinkoth, J. and Wahl, G., Hybridization of nucleic acids immobilized on solid supports, Anal. Biochem., 1984, vol. 138, p. 267-284.
Mojica, FJM, et al., Long stretches of short tandem repeats are present in the largest replicons of the Archaea *Haloferax mediterranei* and *Haloferax volcanii* and could be involved in replicon partitioning, Molecular Microbiology, 1995, 17:85-93.
Myers, E. W. and Miller, W., Optimal alignments in linear space, CABIOS, 1988, 4:11-17.
Nakata, A., et al., Unusual Nucleotide Arrangement with Repeated Sequences in the *Escherichia coli* K-12 Chromosome, J. Bacteriology, 1989, 171, No. 6, p. 3553-3556.
Needleman, S. B. and Wunsch, C. D., A General Method Applicable to the Search for Similarities in the Amino Acid Sequence of Two Proteins, J. Mol. Biol., 1970, vol. 48, p. 443-453.
Pearson, W. R. and Lipman, D. J., Improved tools for biological sequence comparison, Proc. Natl. Acad. Sci. USA, 1988, vol. 85, p. 2444-2448.
Pease, A. C., et al., Light-generated oligonucleotide arrays for rapid DNA sequence analysis, Proc. Natl. Acad. Sci. USA, 1994, vol. 91, No. 11, p. 5022-5026.
Pridmore, R. D., et al., The genome sequence of the probiotic intestinal bacterium *Lactobacillus johnsonii* NCC 533, Proc. Natl. Acad. Sci. U.S.A, 2004, 101:2512-2517.
Roe et al. (1996) DNA Isolation and Sequencing (Essential Techniques Series, John Wiley & Sons).
Sambrook, et al. (1989) Molecular Cloning: A Laboratory Manual, 2d ed., Cold Spring Harbor Laboratory Press, Plainview, N.Y.
Smith, T. F., et al., Comparison of biosequences, Adv. Appl. Math., 1981, vol. 2, p. 482-489.
Tijssen (1993) Laboratory Techniques in Biochemistry and Molecular Biology—Hybridization with Nucleic Acid Probes, Part I, Chapter 2 (Elsevier, N.Y.).
van Belkum, et al., Variable number of tandem repeats in clinical strains of *Haemophilus influenzae*, Infect. Immun., 1997, vol. 65, p. 5017-5027.
van Embden, J.D.A., et al., Strain Identification of *Mycobacterium tuberculosis* by DNA Fingerprinting: Recommendations for a Standardized Methodology, J. Clin. Microbiol., 1993, vol. 31, p. 406-409.
van Embden, J. D. A., et al., Genetic Variation and Evolutionary Origin of the Direct Repeat Locus of *Mycobacterium tuberculosis* Complex Bacteria, J. Bacteriol. 182, No. 9, p. 2393-2401, (2000).
Van Soolingen, D., et al., Comparison of various repetitive DNA elements as genetic markers for strain differentiation and epidemiology of *Mycobacterium tuberculosis*, J. Clin. Microbiol., 1993, 31:1987-1995.
White, P. A., et al., Simplified Hepatitis C Virus Genotyping by Heteroduplex Mobility Analysis, J. Clin. Micro., 2000, vol. 38, No. 2, p. 477-482.

```
aggatcacctccacatacgtggagaaaattggaatctcatcgtaagaaataagtcgcatat
aggatcacctccacatacgtggagaaaatcctttcctaggatcttcataagcttctcgcc
aggatcacctccacatacgtggagaaaatatcgtagtcaatctcgtacttaaaaccaccct
gggatcacctccacatacgtggagaaaatccaggttgacttgcgctaggtgttgcatcaat
aggatcacctccacatacgtggagaaaattaggcaaatagccaatttttatcatacattcc
gggatcacctccacatacgtggagaaaatCGGCAATTTTTGAAACAAACAACTATGTATAT
aggatcacctccacatacgtggagaaaataaataaggaagatattgccaccctcggtaccc
aggatcacctccacatacgtggagaaaatacaagttttgctctaaccatgatgttgtaaac
aggatcacctccacatacgtggagaaaatacgttaaagcggacaataagcttcaacgtttt
aggatcacctccacatacgtggagaaaatcgtgcttgaaattgctctcggggtttcgccta
aggatcacctccacatacgtggagaaaatatttgctgcgagtaactctgacttgtttaccc
gggatcacctccacatacgtggagaaaattttagctaagtttaagaccgaagatggccaaa
gggatcacctccacatacgtggagaaaatCGGCAATTTTTGAAACAAACAACTATGTATAT
aggatcacctccacatacgtggagaaaatCGGCAATTTTTGAAACAAACAACTATGTATAT
aggatcacctccacatacgtggagaaaatacaagttttgctctaaccatgatgttgtaaac
aggatcacctccacatacgtggagaaaatagctatccaaatattaaatttgcactagttaag
gggatcacctccacatacgtggagaaaatgaagaattttatcttctaggtggcttttttgt
gggatcacctccacatacgtggagaaaatagaaatatttgatttgatagtgaaaaagaat
aggatcacctccacatacgtggagaaaattcaagatcaaccattcatttgccacgcaaatc
gggatcacctccacatacgtggagaaaatatttctggtgtgaaaaatgctgatgatatt
gggatcacctccacatacgtggagaaaaccaagatataattaaaagaaaatatcgtagtc
aggatcacctccacatacgtggagaaaactttgatttgagttaagtaccggtgcatcaatg
aggatcacctccacatacgtggagaaaactctttaatgtgaccaaaagcgctcgtagcagc
aggatcacctccacatacgtggagaaaacggacgcaaagggcagaaagctaatttatgac
gggatcacctccacatacgtggagaaaacttgctatgtccgctcttgcttgcattgcagtc
aggatcacctccatatacgtggagaaaacccacgccacatattgtgtgcggaatagcctaa
gggatcacctccacatacgtggagaaaactctgccaaaatagtagccgaatctggaaaatc
aggatcacctccacatacgtggagaaaacaaagtgtcacaaaactagcacctttcattaaa
aggatcacctccacatacgtggagaaaacagagtttagtcgtcgcaatgtgtgtctcaatg
aggatcacctccacatacgtggagaaaactaatacgtaggtggcaagcgttgtccggattt
aggatcacctccacatacgtggagaaaacataaaaataagaggaaaccaccgttttctctt
aggatcacctccacatacgtggagaaaacactaaaggaatcccatcgttaagctattttaa
```

FIG. 2

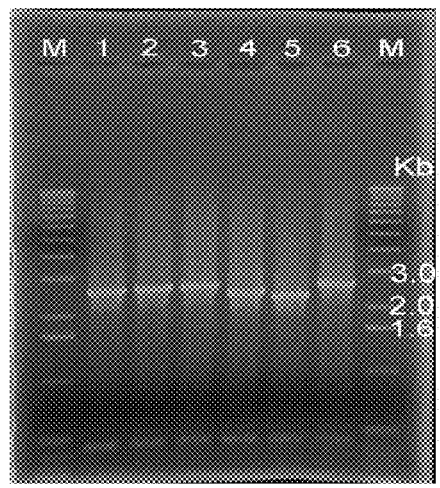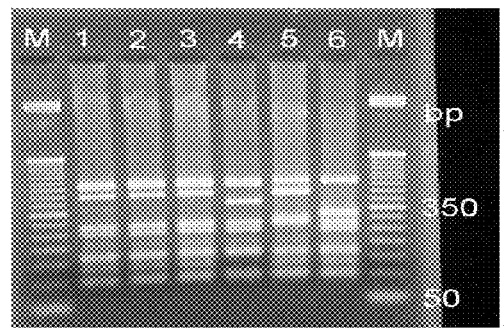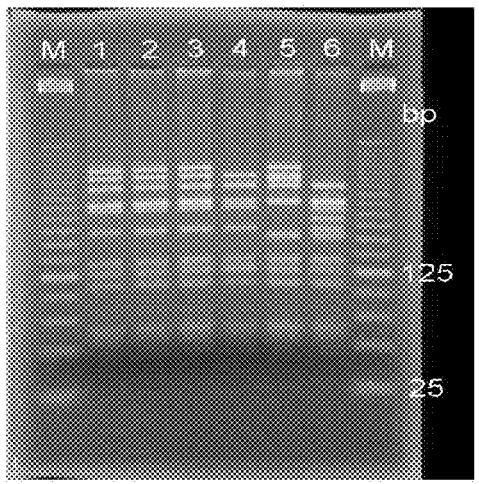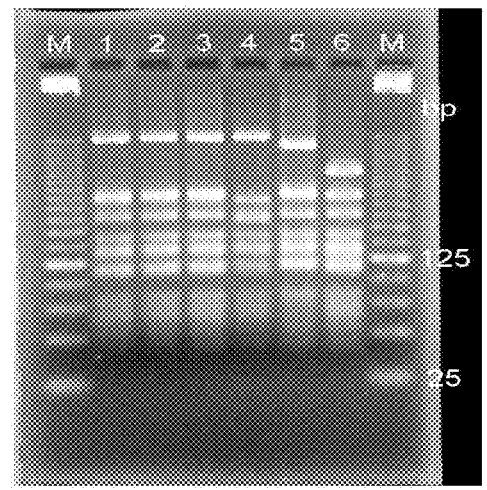
A.
B.
C.
D.
FIG. 3

```
Lac   ATTTTCTCCACGTATGTGGAGGTGATCCT
         G            A  AA                   C

Lbr   GTATACCCCACAGGTGTGGGGGTGATCC
            T        TA  A      CAG AT
                     C          T   TG

Lca   GTTTTCCCCGCACATGCGGGGGTGATCC

Lde   GTATTCCCCACGCAAGTGGGGGTGATCC
                                 GAT
```

FIG. 7

SEQUENCE LISTING

<160> NUMBER OF SEQ ID NOS: 50

<210> SEQ ID NO 1
<211> LENGTH: 1953
<212> TYPE: DNA
<213> ORGANISM: Lactobacillus acidophilus

<400> SEQUENCE: 1

```
aggatcacct ccactttcgt ggagaaaatt ggaatctcat cgtaagaaat aagtcgcata      60
taggatcacc tccacatacg tggagaaaat ccttttccta ggatcttcat aagcttctcg     120
ccaggatcac ctccacatac gtggagaaaa tatcgtagtc aatctcgtac ttaaaaccac     180
cctgggatca cctccacata cgtggagaaa atccaggttg acttgcgcta ggtgttgcat     240
caataggatc acctccacat acgtggagaa aattaggcaa atagccaatt tttatcatac     300
attccgggat cacctccaca tacgtggaga aaatcggcaa tttttgaaac aaacaactat     360
gtatatagga tcacctccac atacgtggag aaaataaata aggaagatat tgccaccctc     420
ggtacccagg atcacctcca catacgtgga gaaaatacaa gttttgctct aaccatgatg     480
ttgtaaacag gatcacctcc acatacgtgg agaaaatacg ttaaagcgga caataagctt     540
caacgtttta ggatcacctc cacatacgtg gagaaaatcg tgcttgaaat tgctctcggg     600
gtttcgccta aggatcacct ccacatacgt ggagaaaata tttgctgcga gtaactctga     660
cttgtttacc cgggatcacc tccacatacg tggagaaaat tttagctaag tttaagaccg     720
aagatggcca aagggatcac ctccacatac gtggagaaaa tcggcaattt ttgaaacaaa     780
caactatgta tataggatca cctccacata cgtggagaaa atcggcaatt tttgaaacaa     840
acaactatgt ataggatc acctccacat acgtggagaa aatacaagtt ttgctctaac     900
catgatgttg taaacaggat cacctccaca tacgtggaga aatagctat ccaaatatta     960 aatttgcact agttaagggg atcacctcca catacgtgga gaaatgaag aattttatct    1020 tctaggtggc tttttttgtgg gatcacctcc acatacgtgg agaaaataga aatatttgat    1080
tttgatagta aaaagaata ggatcacctc cacatacgtg gagaaaattc aagatcaacc    1140
attcatttgc cacgcaaatc gggatcacct ccacatacgt ggagaaaatt attttctggt    1200
gtgaaaaatg ctgatgatat tgggatcacc tccacatacg tggagaaaac ccaagatata    1260
attaaaagaa aatatcgtag tcaggatcac ctccacatac gtggagaaaa ctttgatttg    1320
agttaagtac cggtgcatca atgaggatca cctccacata cgtggagaaa actctttaat    1380
gtgaccaaaa gcgctcgtag cagcaggatc acctccacat acgtggagaa aacggacgca    1440
aaagggcaga aagctaattt atgacgggat cacctccaca tacgtggaga aaacttgcta    1500
tgtccgctct tgcttgcatt gcagtcagga tcacctccat atacgtggag aaaacccacg    1560
ccacatattg tgtgcggaat agcctaaggg atcacctcca catacgtgga gaaactctg    1620 ccaaaatagt agccgaatct ggaaaatcag gatcacctcc acatacgtgg agaaacaaa    1680 gtgtcacaaa actagcacct ttcattaaaa ggatcacctc cacatacgtg gagaaaacag    1740
agtttagtcg tcgcaatgtg tgtctcaatg aggatcacct ccacatacgt ggagaaaact    1800
aatacgtagg tggcaagcgt tgtccggatt taggatcacc tccacatacg tggagaaaac    1860
```

```
ataaaaataa gaggaaacca ccgttttctc ttaggatcac ctccacatac gtggagaaaa    1920
cactaaagga atcccatcgt taagctattt taa                                 1953

<210> SEQ ID NO 2
<211> LENGTH: 29
<212> TYPE: DNA
<213> ORGANISM: Lactobacillus acidophilus

<400> SEQUENCE: 2
aggatcacct ccactttcgt ggagaaaat                                        29

<210> SEQ ID NO 3
<211> LENGTH: 29
<212> TYPE: DNA
<213> ORGANISM: Lactobacillus acidophilus

<400> SEQUENCE: 3
aggatcacct ccacatacgt ggagaaaat                                        29

<210> SEQ ID NO 4
<211> LENGTH: 29
<212> TYPE: DNA
<213> ORGANISM: Lactobacillus acidophilus

<400> SEQUENCE: 4
gggatcacct ccacatacgt ggagaaaat                                        29

<210> SEQ ID NO 5
<211> LENGTH: 29
<212> TYPE: DNA
<213> ORGANISM: Lactobacillus acidophilus

<400> SEQUENCE: 5
gggatcacct ccacatacgt ggagaaaac                                        29

<210> SEQ ID NO 6
<211> LENGTH: 29
<212> TYPE: DNA
<213> ORGANISM: Lactobacillus acidophilus

<400> SEQUENCE: 6
aggatcacct ccacatacgt ggagaaaac                                        29

<210> SEQ ID NO 7
<211> LENGTH: 29
<212> TYPE: DNA
<213> ORGANISM: Lactobacillus acidophilus

<400> SEQUENCE: 7
aggatcacct ccacatacgt ggagaaaac                                        29

<210> SEQ ID NO 8
<211> LENGTH: 32
<212> TYPE: DNA
<213> ORGANISM: Lactobacillus acidophilus

<400> SEQUENCE: 8
tggaatctca tcgtaagaaa taagtcgcat at                                    32

<210> SEQ ID NO 9
<211> LENGTH: 32
<212> TYPE: DNA
<213> ORGANISM: Lactobacillus acidophilus
```

```
<400> SEQUENCE: 9
ccttttccta ggatcttcat aagcttctcg cc                                    32

<210> SEQ ID NO 10
<211> LENGTH: 32
<212> TYPE: DNA
<213> ORGANISM: Lactobacillus acidophilus

<400> SEQUENCE: 10
atcgtagtca atctcgtact taaaaccacc ct                                    32

<210> SEQ ID NO 11
<211> LENGTH: 32
<212> TYPE: DNA
<213> ORGANISM: Lactobacillus acidophilus

<400> SEQUENCE: 11
ccaggttgac ttgcgctagg tgttgcatca at                                    32

<210> SEQ ID NO 12
<211> LENGTH: 32
<212> TYPE: DNA
<213> ORGANISM: Lactobacillus acidophilus

<400> SEQUENCE: 12
taggcaaata gccaattttt atcatacatt cc                                    32

<210> SEQ ID NO 13
<211> LENGTH: 32
<212> TYPE: DNA
<213> ORGANISM: Lactobacillus acidophilus

<400> SEQUENCE: 13
cggcaatttt tgaaacaaac aactatgtat at                                    32

<210> SEQ ID NO 14
<211> LENGTH: 32
<212> TYPE: DNA
<213> ORGANISM: Lactobacillus acidophilus

<400> SEQUENCE: 14
aaataaggaa gatattgcca ccctcggtac cc                                    32

<210> SEQ ID NO 15
<211> LENGTH: 32
<212> TYPE: DNA
<213> ORGANISM: Lactobacillus acidophilus

<400> SEQUENCE: 15
acaagttttg ctctaaccat gatgttgtaa ac                                    32

<210> SEQ ID NO 16
<211> LENGTH: 32
<212> TYPE: DNA
<213> ORGANISM: Lactobacillus acidophilus

<400> SEQUENCE: 16
acgttaaagc ggacaataag cttcaacgtt tt                                    32

<210> SEQ ID NO 17
<211> LENGTH: 32
<212> TYPE: DNA
<213> ORGANISM: Lactobacillus acidophilus
```

```
<400> SEQUENCE: 17
cgtgcttgaa attgctctcg gggtttcgcc ta                                    32

<210> SEQ ID NO 18
<211> LENGTH: 32
<212> TYPE: DNA
<213> ORGANISM: Lactobacillus acidophilus

<400> SEQUENCE: 18
atttgctgcg agtaactctg acttgtttac cc                                    32

<210> SEQ ID NO 19
<211> LENGTH: 32
<212> TYPE: DNA
<213> ORGANISM: Lactobacillus acidophilus

<400> SEQUENCE: 19
tttagctaag tttaagaccg aagatggcca aa                                    32

<210> SEQ ID NO 20
<211> LENGTH: 33
<212> TYPE: DNA
<213> ORGANISM: Lactobacillus acidophilus

<400> SEQUENCE: 20
agctatccaa atattaaatt tgcactagtt aag                                   33

<210> SEQ ID NO 21
<211> LENGTH: 32
<212> TYPE: DNA
<213> ORGANISM: Lactobacillus acidophilus

<400> SEQUENCE: 21
gaagaatttt atcttctagg tggcttttttt gt                                   32

<210> SEQ ID NO 22
<211> LENGTH: 32
<212> TYPE: DNA
<213> ORGANISM: Lactobacillus acidophilus

<400> SEQUENCE: 22
agaaatattt gattttgata gtgaaaaaga at                                    32

<210> SEQ ID NO 23
<211> LENGTH: 32
<212> TYPE: DNA
<213> ORGANISM: Lactobacillus acidophilus

<400> SEQUENCE: 23
tcaagatcaa ccattcattt gccacgcaaa tc                                    32

<210> SEQ ID NO 24
<211> LENGTH: 32
<212> TYPE: DNA
<213> ORGANISM: Lactobacillus acidophilus

<400> SEQUENCE: 24
tattttctgg tgtgaaaaat gctgatgata tt                                    32

<210> SEQ ID NO 25
<211> LENGTH: 32
<212> TYPE: DNA
<213> ORGANISM: Lactobacillus acidophilus
```

```
<400> SEQUENCE: 25
ccaagatata attaaaagaa aatatcgtag tc                                      32

<210> SEQ ID NO 26
<211> LENGTH: 32
<212> TYPE: DNA
<213> ORGANISM: Lactobacillus acidophilus

<400> SEQUENCE: 26
tttgatttga gttaagtacc ggtgcatcaa tg                                      32

<210> SEQ ID NO 27
<211> LENGTH: 32
<212> TYPE: DNA
<213> ORGANISM: Lactobacillus acidophilus

<400> SEQUENCE: 27
tctttaatgt gaccaaaagc gctcgtagca gc                                      32

<210> SEQ ID NO 28
<211> LENGTH: 32
<212> TYPE: DNA
<213> ORGANISM: Lactobacillus acidophilus

<400> SEQUENCE: 28
ggacgcaaaa gggcagaaag ctaatttatg ac                                      32

<210> SEQ ID NO 29
<211> LENGTH: 32
<212> TYPE: DNA
<213> ORGANISM: Lactobacillus acidophilus

<400> SEQUENCE: 29
ttgctatgtc cgctcttgct tgcattgcag tc                                      32

<210> SEQ ID NO 30
<211> LENGTH: 32
<212> TYPE: DNA
<213> ORGANISM: Lactobacillus acidophilus

<400> SEQUENCE: 30
ccacgccaca tattgtgtgc ggaatagcct aa                                      32

<210> SEQ ID NO 31
<211> LENGTH: 32
<212> TYPE: DNA
<213> ORGANISM: Lactobacillus acidophilus

<400> SEQUENCE: 31
tctgccaaaa tagtagccga atctggaaaa tc                                      32

<210> SEQ ID NO 32
<211> LENGTH: 32
<212> TYPE: DNA
<213> ORGANISM: Lactobacillus acidophilus

<400> SEQUENCE: 32
aaagtgtcac aaaactagca cctttcatta aa                                      32

<210> SEQ ID NO 33
<211> LENGTH: 32
<212> TYPE: DNA
<213> ORGANISM: Lactobacillus acidophilus
```

```
<400> SEQUENCE: 33
agagtttagt cgtcgcaatg tgtgtctcaa tg                                32

<210> SEQ ID NO 34
<211> LENGTH: 32
<212> TYPE: DNA
<213> ORGANISM: Lactobacillus acidophilus

<400> SEQUENCE: 34
taatacgtag gtggcaagcg ttgtccggat tt                                32

<210> SEQ ID NO 35
<211> LENGTH: 32
<212> TYPE: DNA
<213> ORGANISM: Lactobacillus acidophilus

<400> SEQUENCE: 35
ataaaaataa gaggaaacca ccgttttctc tt                                32

<210> SEQ ID NO 36
<211> LENGTH: 32
<212> TYPE: DNA
<213> ORGANISM: Lactobacillus acidophilus

<400> SEQUENCE: 36
actaaaggaa tcccatcgtt aagctatttt aa                                32

<210> SEQ ID NO 37
<211> LENGTH: 29
<212> TYPE: DNA
<213> ORGANISM: Lactobacillus acidophilus

<400> SEQUENCE: 37
attttctcca cgtatgtgga ggtgatcct                                    29

<210> SEQ ID NO 38
<211> LENGTH: 28
<212> TYPE: DNA
<213> ORGANISM: Lactobacillus brevis

<400> SEQUENCE: 38 gtataccccca caggtgtggg ggtgatcc                                    28

<210> SEQ ID NO 39
<211> LENGTH: 27
<212> TYPE: DNA
<213> ORGANISM: Lactobacillus brevis

<400> SEQUENCE: 39
gtattcccca cacgtgtggg ggtgatc                                      27

<210> SEQ ID NO 40
<211> LENGTH: 28
<212> TYPE: DNA
<213> ORGANISM: Lactobacillus brevis

<400> SEQUENCE: 40
gtattcccca cacatgtggg ggtgatcc                                     28

<210> SEQ ID NO 41
<211> LENGTH: 28
<212> TYPE: DNA
<213> ORGANISM: Lactobacillus brevis
```

```
<400> SEQUENCE: 41
gtattcccca catatgtagg ggtggtct                                             28

<210> SEQ ID NO 42
<211> LENGTH: 28
<212> TYPE: DNA
<213> ORGANISM: Lactobacillus brevis

<400> SEQUENCE: 42
gtattcccca caggtgtggg ggtaatag                                             28

<210> SEQ ID NO 43
<211> LENGTH: 28
<212> TYPE: DNA
<213> ORGANISM: Lactobacillus brevis

<400> SEQUENCE: 43
gtattcccca caggtgtggg ggtgatcc                                             28

<210> SEQ ID NO 44
<211> LENGTH: 28
<212> TYPE: DNA
<213> ORGANISM: Lactobacillus brevis

<400> SEQUENCE: 44
gtatacccca caggtgtggg ggcatttc                                             28

<210> SEQ ID NO 45
<211> LENGTH: 28
<212> TYPE: DNA
<213> ORGANISM: Lactobacillus casei

<400> SEQUENCE: 45
gttttccccg cacatgcggg ggtgatcc                                             28

<210> SEQ ID NO 46
<211> LENGTH: 28
<212> TYPE: DNA
<213> ORGANISM: Lactobacillus delbrueckii

<400> SEQUENCE: 46
gtattcccca cgcaagtggg ggtgatcc                                             28

<210> SEQ ID NO 47
<211> LENGTH: 28
<212> TYPE: DNA
<213> ORGANISM: Lactobacillus delbrueckii

<400> SEQUENCE: 47
gtattcccca cgcaagtggg ggtgatcc                                             28

<210> SEQ ID NO 48
<211> LENGTH: 28
<212> TYPE: DNA
<213> ORGANISM: Lactobacillus delbrueckii

<400> SEQUENCE: 48
gtattcccca cgcaagtggg ggtggatc                                             28

<210> SEQ ID NO 49
<211> LENGTH: 23
<212> TYPE: DNA
<213> ORGANISM: Lactobacillus acidophilus
```

```
<400> SEQUENCE: 49
gcattagtgt gcaacccatc tgg                                        23

<210> SEQ ID NO 50
<211> LENGTH: 23
<212> TYPE: DNA
<213> ORGANISM: Lactobacillus acidophilus

<400> SEQUENCE: 50
gatctgctgg attgcttcta ccg                                        23
```

DETECTION AND TYPING OF BACTERIAL STRAINS

CROSS REFERENCE TO RELATED APPLICATIONS

This application is a divisional application of U.S. patent application Ser. No. 11/115,873, filed Apr. 27, 2005, which claims the benefit of U.S. Provisional Patent Application Ser. No. 60/566,007, filed Apr. 28, 2004, the contents of which are hereby incorporated in their entirety by reference herein.

FIELD OF THE INVENTION

This invention relates to methods for detecting and typing bacterial strains, specifically *Lactobacillus* strains.

BACKGROUND OF THE INVENTION

Rapid and accurate differentiation of bacterial strains is important when making medical diagnoses, in epidemiological studies, and for studying evolutionary diversity among bacteria. Various methods exist for typing or detecting bacterial strains, including RFLP, hybridization, and sequencing. Epidemiologically informative microsatellite DNA polymorphisms have been observed in different strains of *Helicobacter pylori* (Marshall et al. (1996) *J. Appl. Bacteria* 81:509-517). Similarly, repetitive DNA elements of *Mycobacterium tuberculosis* have been used for efficient strain tracking (Van Soolingen et al. (1993) *J. Clin. Microbiol.* 31:1987-1995). In addition, short sequence repeat (SSR) variation has been used to differentiate the strains of *Haemophilus influenzae* isolated from different patients (van Belkum et al. (1997) *Infect. Immun.* 65:5017-5027). However, current methods available to specifically differentiate bacterial strains, such as *Lactobacillus acidophilus* strains, are based either on 16SrRNA gene sequencing, which is only accurate to the species level, or on long and difficult Pulsed Field Gel Electrophoresis (PFGE) procedures.

The CRISPR (Clustered Regularly Interspaced Short Palindromic Repeat; also called SPIDR (Spacers Interspersed Direct Repeats), VNTR (Variable Number of Tandem Repeats), SRVR (Short Regularly Variable Repeats), and SRSR (Short Regularly Spaced Repeats)) loci, described by Jansen et al. (2002) *OMICS J. Integr. Biol.* 6:23-33, constitute a novel family of repeat sequences that is present in *Bacteria* and *Archaea* but not in *Eukarya*. The repeat loci typically consist of repetitive stretches of nucleotides with a length of 25 to 37 base pairs alternated by nonrepetitive DNA spacers of approximately equal length. To date, CRISPR loci have been identified in more than forty microorganisms (Jansen et al. (2002) *OMICS J. Integr. Biol.* 6:23-33), but from the lactic acid bacteria, they have only been described from *Streptococcus* species. Despite their discovery over 15 years ago in *E. coli* (Ishino et al. (1987) *J. Bacteria* 169:5429-5433), no physiological function has yet been discovered. The nucleotide sequences of the repeats are generally highly conserved within a species, but show low similarity between species. It has also been shown that variability among CRISPR loci is not due primarily to single nucleotide base changes, but rather to deletions/insertions of entire repeat and spacer regions. These properties have led to the use of the CRISPR loci as a strain-typing tool in *Mycobacterium* (Groenen et al. (1993) *Mol. Microbiol.* 10:1057-1065).

As methods to differentiate *Lactobacillus* bacteria, specifically *L. acidophilus*, are either not accurate to the strain level or are technically demanding, the development of new methods for differentiating *Lactobacillus* strains is desirable.

BRIEF SUMMARY OF THE INVENTION

Compositions and methods for detecting and typing bacteria are provided, particularly a *Lactobacillus* strain of bacteria, for example a *Lactobacillus acidophilus* strain. Compositions of the invention include isolated nucleic acid molecules from *Lactobacillus acidophilus* comprising a region of DNA, preferably located between the genes for DNA polymerase I (polA) and a putative phosphoribosylamine-glycine ligase (purD), consisting of one or more copies of a repetitive DNA sequence of about 20-40 base pairs, such as about 25-35 base pairs or of about 27-30 base pairs, interspersed with nonrepetitive spacer sequences of about the same length. In one embodiment, the isolated nucleic acid molecule comprises a 29 base pair sequence that is present 32 times, and is separated by the same number of 32-base pair spacer sequences.

Compositions of the invention also include isolated nucleic acid molecules from *Lactobacillus brevis*, *Lactobacillus casei*, and *Lactobacillus delbrueckii* ssp. *bulgaricus* comprising repetitive sequences originally identified in a CRISPR region. In one embodiment, the isolated nucleic acid molecule comprises a 28 base pair sequence from *L. brevis*. In another embodiment, the isolated nucleic acid molecule comprises a 28 base pair sequence from *L. casei*. In yet another embodiment, the isolated nucleic acid molecule comprises a 28 base pair sequence from *L. delbrueckii* ssp. *bulgaricus*.

Variant nucleic acid molecules sufficiently identical to the nucleotide sequences are also encompassed by the present invention. Additionally, fragments and sufficiently identical fragments of the nucleotide sequences are encompassed. Specifically, the present invention provides for isolated nucleic acid molecules comprising one or more nucleotide sequences found in SEQ ID NOS:1-50. The present invention further provides for isolated nucleic acid molecules comprising 1-140 repeats of a nucleotide sequence of the invention, or a variant thereof. In some embodiments, the isolated nucleic acid molecules comprise more than 5 repeats, more than 10 repeats, less than 50 repeats, or less than 35 repeats of a nucleotide sequence of the invention, or a variant thereof. Compositions also include PCR primers for amplifying this region in a *Lactobacillus* species, including *L. acidophilus*, *L. brevis*, *L. casei* and *L. delbrueckii*. Nucleotide sequences that are complementary to a nucleotide sequence of the invention, or that hybridize to a sequence of the invention, are also encompassed. Further are included methods and kits for detecting the presence of a nucleic acid sequence of the invention in a sample, and methods and kits for typing bacteria, including *Lactobacillus* strains, particularly *L. acidophilus*, *L. brevis*, *L. casei* and *L. delbrueckii* strains.

Methods for typing a bacterium having a CRISPR region are provided. The methods comprise obtaining a sample comprising the bacterium; amplifying a region of DNA comprising the CRISPR region or a fragment thereof in the sample to create amplified DNA; adding to the amplified DNA at least one restriction enzyme that recognizes one or more sites in the amplified DNA; incubating the restriction enzyme with the amplified DNA for a time sufficient to form restriction fragments; determining the number of the restriction fragments and their size; and typing the bacterium based on the number and size of the restriction fragments.

A method for typing a *Lactobacillus* bacterial strain is also provided. The method comprises obtaining a sample, amplifying a region of DNA comprising at least one of the nucleotide sequences set forth in SEQ ID NOS:1-7 and 37-48, or a variant thereof, in the sample to create amplified DNA, and typing the bacterial strain based on the amplified DNA. The methods may further comprise adding to the amplified DNA at least one restriction enzyme that recognizes one or more sites in the amplified DNA, incubating the restriction enzyme with the amplified DNA for a time sufficient to form restriction fragments, determining the number of the restriction fragments and their size, and typing the bacterial strain based on the number and size of the restriction fragments. Alternatively, the methods may further comprise sequencing the amplified DNA to obtain sequencing results, and typing the bacterial strain based on the sequencing results. In one embodiment, the *Lactobacillus* is *L. acidophilus*.

The amplified DNA may be obtained by providing a first primer that binds to a repetitive sequence in a CRISPR region, providing a second primer that binds to DNA flanking (i.e., upstream or downstream of) the CRISPR region, using the primers in a PCR reaction to create amplified DNA, separating the amplified DNA on a gel to produce a distinct band pattern showing the number and sizes of the amplified DNA, and typing the bacterial strain based on the band pattern. The number and sizes of the bands are characteristic of the strain. The amplified DNA may alternatively be obtained by providing a first primer that binds to a region of DNA upstream of the CRISPR region, and a second primer that binds to a region of DNA downstream of the CRISPR region, using the primers in a PCR reaction to create amplified DNA, separating the amplified DNA on a gel to produce a band showing the size of the amplified CRISPR DNA, and typing the bacterial strain based on the band size. The size of the amplified DNA is characteristic of the strain.

Methods for detecting the presence of a *Lactobacillus* species in a sample are provided. The methods comprise obtaining a sample, amplifying a region of DNA comprising at least one of the nucleotide sequences set forth in SEQ ID NOS:1-7 and 37-48, or a variant thereof, to create amplified DNA, and detecting the amplified DNA. The methods may further comprise adding to the amplified DNA at least one restriction enzyme that recognizes one or more sites in the amplified DNA, incubating the restriction enzyme with the amplified DNA for a time sufficient to form restriction fragments, determining the number of the restriction fragments and their size, and detecting the presence of a *Lactobacillus* species based on the number and size of the restriction fragments. Alternatively, the methods may further comprise sequencing the amplified DNA to obtain sequencing results, and detecting the presence of a *Lactobacillus* species based on the sequencing results.

The methods of the present invention are useful for the detection and typing of bacterial strains, including *Lactobacillus* strains such as *L. acidophilus, L. brevis, L. casei*, and *L. delbrueckii* strains, in food products and dietary supplements, including animal feed and animal feed supplements, in in vivo/in vitro samples, and for studying the natural diversity of the species from environmental samples. The methods are also useful for product development and identification of new bacterial strains, particularly *Lactobacillus* strains.

BRIEF DESCRIPTION OF THE DRAWINGS

FIG. 2 shows the nucleotide sequences of the repeat regions in the intergenic region (SEQ ID NO:1). The 29-bp repeats are highlighted (SEQ ID NOS:2-7). An imperfect inverted repeat is indicated by an underline on the last repeat. The spacer regions (SEQ ID NOS:8-35) and a flanking region (SEQ ID NO:36) are not highlighted. Two sequences are repeated in the spacer region; one is repeated twice (outlined and bold) (SEQ ID NO:15) and one is repeated three times (caps and bold) (SEQ ID NO:13).

FIG. 3 consists of micrographs of various agarose gel electrophoresis experiments. FIG. 3A shows PCR products and FIGS. 3B, C, and D show restriction fragment results. A. Lane M-1 Kb DNA ladder; Lane 1-NCFM®; Lane 2-Strain C; Lane 3-Strain D; Lane 4-ATCC 4356; Lane 5-Strain B; Lane 6-Strain E. B. Lane M-50 bp DNA ladder; Lane 1-NCFM®; Lane 2-Strain C; Lane 3-Strain D; Lane 4-ATCC 4356; Lane 5-ATCC 4357; Lane 6-Strain B. C. Lane M-50 bp DNA ladder; Lane 1-NCFM®; Lane 2-Strain C; Lane 3-Strain D; Lane 4-ATCC 4356; Lane 5-ATCC 4357; Lane 6-Strain B. D. Lane M-50 bp DNA ladder; Lane 1-NCFM®; Lane 2-Strain C; Lane 3-Strain D; Lane 4-ATCC 4356; Lane 5-ATCC 4357; Lane 6-Strain B.

FIG. 7 shows a repeat sequence from *L. acidophilus* (Lac) (SEQ ID NO:37); *L. brevis* (Lbr) (SEQ ID NO:38); *L. casei* (Lca) (SEQ ID NO:45); and *L. delbrueckii* ssp. *Bulgaricus* (Lde) (SEQ ID NO:46). Variant nucleotides and their positions are shown below the main sequence.

DETAILED DESCRIPTION OF THE INVENTION

Figure 1:
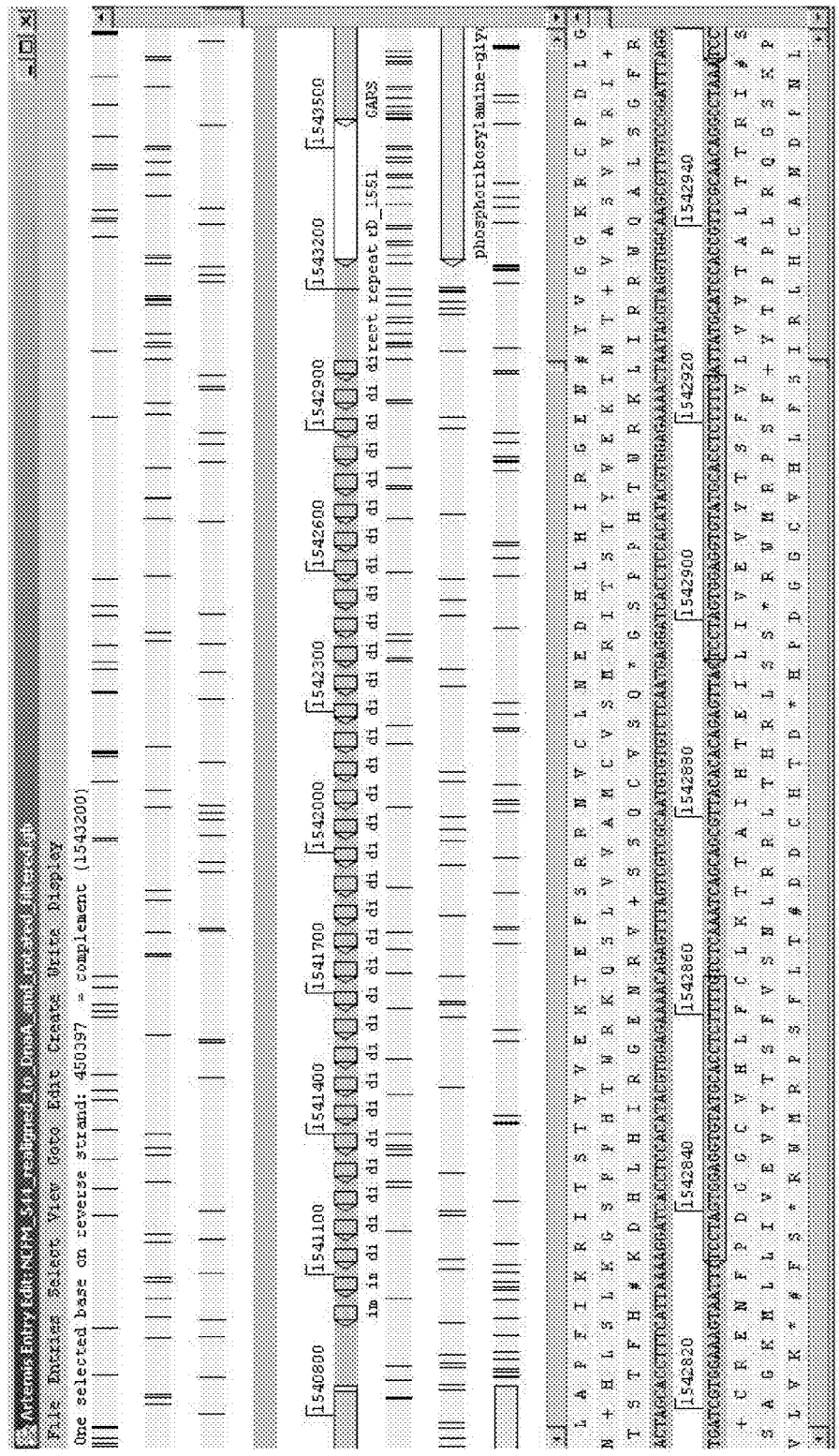
FIG. 1 shows an intergenic region in *Lactobacillus acidophilus* having features of a CRISPR locus.

The present invention relates to methods and compositions for detecting and/or typing bacterial strains, such as *Lactobacillus* strains, including *Lactobacillus acidophilus, L. brevis, L. casei*, and *L. delbrueckii*. These methods can be used in medical and food safety diagnostics, or in research. By "typing" or "differentiation" is intended the identification of the strain of a bacterium, including identifying that it is distinct from other strains based on its nucleotide sequence (i.e., by analyzing the band pattern resulting from restriction enzyme digestion). By "detection" is intended the verification of the presence or absence of a species of bacteria in a sample.

Compositions of the invention include isolated nucleic acid molecules from *L. acidophilus, L. brevis, L. casei*, and *L. delbrueckii* that are part of a CRISPR locus. By "CRISPR region" or "CRISPR locus" is intended a repetitive stretch of nucleotide sequence, wherein the repeats are about 20 to about 40 base pairs in length, and are alternated by nonrepetitive DNA spacers of approximately equal size. The acronyms CRISPR, SPIDR, VNTR, and SRVR have each been used to describe a nucleotide sequence having interspaced repeats.

Additionally, the present invention provides methods and kits for bacterial typing that may be used to determine similarities and/or differences between bacterial strains, particularly *Lactobacillus* strains, including *L. acidophilus, L. brevis, L. casei*, and *L. delbrueckii*, and methods and kits for detecting the presence or absence of a *Lactobacillus* species in a sample. More particularly, the methods involve a rapid, semi-automated method for the detection and/or typing of strains of prokaryotic organisms, such as *L. acidophilus*, in which a CRISPR DNA sequence is amplified and used to differentiate between strains of *Lactobacillus*, or for the detection of a *Lactobacillus* species.

Isolated nucleic acid molecules of the present invention comprise the nucleotide sequences set forth in SEQ ID NOS: 1-50, and variants and fragments thereof. The present invention also encompasses molecules that are complementary to these nucleic acid sequences, or that hybridize to these sequences.

The nucleic acid compositions encompassed by the present invention are isolated or substantially purified. By "isolated" or "substantially purified" is intended that the nucleic acid molecules, or biologically active fragments or variants, are substantially or essentially free from components normally found in association with the nucleic acid in its natural state. Such components include other cellular material, culture media from recombinant production, and various chemicals used in chemically synthesizing the nucleic acids. Preferably, an "isolated" nucleic acid of the present invention is free of nucleic acid sequences that flank the nucleic acid of interest in the genomic DNA of the organism from which the nucleic acid was derived (such as coding sequences present at the 5' or 3' ends). However, the molecule may include some additional bases or moieties that do not deleteriously affect the basic characteristics of the composition. For example, in various embodiments, the isolated nucleic acid contains less than 5 kb, 4 kb, 3 kb, 2 kb, 1 kb, 0.5 kb, or 0.1 kb of nucleic acid sequence normally associated with the genomic DNA in the cells from which it was derived.

The compositions and methods of the present invention can be used to detect *Lactobacillus* species, including *L. acidophilus, L. brevis, L. casei*, and *L. delbrueckii*, or to type bacterial strains, including very closely related *L. acidophilus* strains, both in the laboratory and in commercial products. This is useful for product development, as well as for research in bacterial species diversity and evolution, and in the identification of new bacterial strains, including new *Lactobacillus* strains.

Detection and Differentiation of Bacterial Strains

CRISPR loci are a distinct class of interspersed short sequence repeats (SSRs) that were first recognized in *E. coli* (Ishino et al. (1987) *J. Bacteriol.* 169:5429-5433; Nakata et al. (1989) *J. Bacteriol.* 171:3553-3556). Similar interspersed SSRs have been identified in *Haloferax mediterranei, Streptococcus pyogenes, Anabaena*, and *Mycobacterium tuberculosis* (Groenen et al. (1993) *Mol. Microbiol.* 10:1057-1065; Hoe et al. (1999) *Emerg. Infect. Dis.* 5:254-263; Masepohl et al. (1996) *Biochim. Biophys. Acta* 1307:26-30; Mojica et al. (1995) *Mol. Microbiol.* 17:85-93). The CRISPR loci differ from other SSRs by the structure of the repeats, which have been termed short regularly spaced repeats (SRSRs) (Janssen et al. (2002) *OMICS J. Integ. Biol.* 6:23-33; Mojica et al. (2000) *Mol. Microbiol.* 36:244-246). The repeats are short elements that occur in clusters, that are always regularly spaced by unique intervening sequences with a constant length (Mojica et al. (2000) *Mol. Microbiol.* 36:244-246). Although the repeat sequences are highly conserved between strains, the number of interspersed repeats and the sequences of the spacer regions differ from strain to strain (van Embden et al. (2000) *J. Bacteriol.* 182:2393-2401). Methods for identifying CRISPR regions are well known in the art (see, for example, the above references, which are incorporated by reference herein in their entirety, as well as the methods used in Example 1). The methods of the present invention are herein exemplified by experiments involving *L. acidophilus*; however, one of skill in the art would recognize that the methods may be used for detection and/or strain identification of any bacterium having a CRISPR region.

The number of nucleotides in a repeat is generally about 20 to about 40 base pairs, but may be about 20 to about 39 base pairs, about 20 to about 37 base pairs, about 20 to about 35 base pairs, about 20 to about 33 base pairs, about 20 to about 30 base pairs, about 21 to about 40 base pairs, about 21 to about 39 base pairs, about 21 to about 37 base pairs, about 23 to about 40 base pairs, about 23 to about 39 base pairs, about 23 to about 37 base pairs, about 25 to about 40 base pairs, about 25 to about 39 base pairs, about 25 to about 37 base pairs, about 25 to about 35 base pairs, or about 28 or 29 base pairs. The number of repeats may range from about 1 to about 140, from about 1 to about 100, from about 2 to about 100, from about 5 to about 100, from about 10 to about 100, from about 15 to about 100, from about 20 to about 100, from about 25 to about 100, from about 30 to about 100, from about 35 to about 100, from about 40 to about 100, from about 45 to about 100, from about 50 to about 100, from about 1 to about 135, from about 1 to about 130, from about 1 to about 125, from about 1 to about 120, from about 1 to about 115, from about 1 to about 110, from about 1 to about 105, from about 1 to about 100, from about 1 to about 95, from about 1 to about 90, from about 1 to about 80, from about 1 to about 70, from about 1 to about 60, from about 1 to about 50, from about 10 to about 140, from about 10 to about 130, from about 10 to about 120, from about 10 to about 110, from about 10 to about 95, from about 10 to about 90, from about 20 to about 80, from about 30 to about 70, from about 30 to about 60, from about 30 to about 50, from about 30 to about 40, or about 32.

The nucleotide sequences disclosed herein may be used to detect *Lactobacillus* species, and/or to differentiate bacterial strains, including differentiating *L. acidophilus* NCFM® strains from other *L. acidophilus* strains. The detection and/or differentiation is based on the identification of novel CRISPR regions in *L. acidophilus* NCFM®, *L. brevis, L. casei*, and *L. delbrueckii* subspecies *bulgaricus*. As these CRISPR regions are strain-specific, any method assaying for the presence of these specific sequences is encompassed by the current invention. The present invention is applicable to medical testing, food testing, agricultural testing, and environmental testing.

Diagnostic assays to detect the presence of a nucleic acid molecule in a sample are disclosed. These methods comprise obtaining a sample, amplifying a region of DNA comprising at least one of SEQ ID NOS:1-7 and 37-48, or a variant thereof, to create amplified DNA, and detecting the amplified DNA. Detection of amplified DNA is specific for a *Lactobacillus* species. Different strains of a species of *Lactobacillus*, such as a *L. acidophilus* species, may have different sizes of amplified DNA. Therefore, this method may also be used as a tool for strain differentiation. The method may further comprise sequencing the amplified DNA and detecting the presence of a *Lactobacillus* species, such as *L. acidophilus, L. brevis, L. casei*, or *L. delbrueckii*, based on the sequencing results. Alternatively, the method may further comprise adding to the amplified DNA at least one restriction enzyme that recognizes one or more sites in the amplified DNA, incubating the restriction enzyme with the amplified DNA for a time sufficient to form restriction fragments, determining the number and size of the restriction fragments, and detecting the presence of a *Lactobacillus* species, such as *L. acidophilus, L. brevis, L. casei*, or *L. delbrueckii*, based on the number and size of the restriction fragments.

Methods for typing a *Lactobacillus* bacterial strain are provided. These methods comprise obtaining a sample, amplifying a region of DNA comprising at least one of the nucleotide sequences set forth in SEQ ID NOS:1-7 and 37-48, or a variant thereof, in the sample to create amplified DNA, and typing the bacterial strain based on the amplified DNA. This typing may be done by adding to the amplified DNA at least one restriction enzyme that recognizes one or more sites in the amplified DNA, incubating the restriction enzyme with the amplified DNA for a time sufficient to form restriction fragments, determining the number of the restriction fragments and their size, and typing the bacterial strain based on the number and size of the restriction fragments. Typing may also be done by sequencing the amplified DNA, and typing the bacterial strain based on the sequencing results. In one embodiment, the region of DNA to be amplified comprises SEQ ID NO:1. In another embodiment, the region of DNA comprises a nucleotide sequence having at least 75% sequence identity to at least one of SEQ ID NOS:1-7 and 37-48.

The amplified DNA may be obtained by providing a first primer that binds to a region of DNA flanking the CRISPR region, such as DNA upstream of the CRISPR region, and a second primer that binds to a region of DNA flanking the CRISPR region, such as DNA downstream of the CRISPR region; using the primers in a PCR reaction to create amplified DNA; separating the amplified DNA on a gel to produce a band showing the size of the amplified CRISPR DNA; and typing the bacterial strain based on the band size. The size of the amplified DNA is characteristic of the strain of *Lactobacillus*. In one embodiment, the first primer binds to a region of DNA upstream of the CRISPR region, such as that set forth in SEQ ID NO:49, and the second primer binds to a region of DNA downstream of the CRISPR region, such as that set forth in SEQ ID NO:50.

Alternatively, the amplified DNA may be obtained by providing a first primer that binds to a repetitive sequence in a CRISPR region; providing a second primer that binds to DNA flanking (i.e. upstream or downstream of) the CRISPR region; using the primers in a PCR reaction to create amplified DNA; separating the amplified DNA on a gel to produce a distinct band pattern showing the number and sizes of the amplified DNA; and typing the bacterial strain based on the pattern. The number and sizes of the bands are diagnostic of the strain of *Lactobacillus*. In one embodiment, the first primer binds to any of SEQ ID NOS:2-7 and 37-48, and the second primer binds to DNA flanking any of SEQ ID NOS: 2-7 and 37-48.

This method wherein one primer binds to any of SEQ ID NOS:2-7 and 37-48 produces a number of bands of varying sizes, depending on the number and spacing of the repeats in relation to the anchored primer. For example, if the repeat region is present five times, the primer complementary to the repeat region will bind in five places and generate five bands that may be visualized as a fingerprint on an agarose or polyacrylamide gel. The PCR products may be amplified to different extents, and some of the resulting bands may therefore not be visualized as easily as others, if at all. The distinct band pattern shows the number and size of the amplified DNA, and may be used to characterize *Lactobacillus* strains, including *L. acidophilus, L. brevis, L. casei*, and *L. delbrueckii* strains.

The term "sample" is intended to include tissues, cells, and biological fluids present in or isolated from a subject, as well as cells from starter cultures (mother, seed, bulk/set, concentrated, dried, lyophilized, frozen), or food/dairy/feed products carrying such cultures, or derived from the use of such cultures. The sample may be a dietary supplement, bioprocessing fermentate, or a subject that has ingested a substance comprising the nucleotide sequence. That is, the detection method of the invention can be used to detect genomic DNA comprising a disclosed nucleotide sequence in a sample both in vitro and in vivo. In vitro techniques for detection of genomic DNA comprising the disclosed nucleotide sequences include, but are not limited to, Southern hybridizations. Results obtained with a sample from the food, supplement, culture, product, or subject may be compared to results obtained with a sample from a control culture, product, or subject. In one embodiment, the sample contains genomic DNA from a starter culture.

Amplification of the desired region of DNA may be achieved by any method known in the art, including polymerase chain reaction (PCR). By "amplification" is intended the production of additional copies of a nucleic acid sequence. This is generally carried out using PCR technologies well known in the art (Dieffenbach and Dveksler (1995) *PCR Primer, a Laboratory Manual* (Cold Spring Harbor Press, Plainview, N.Y.). By "polymerase chain reaction" or "PCR" is intended a method such as that disclosed in U.S. Pat. Nos. 4,683,195 and 4,683,202, herein incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as "PCR". Because the desired amplified segments of the target sequence become the predominant sequences (in terms of concentration) in the mixture, they are said to be "PCR amplified."

In a PCR approach, oligonucleotide primers can be designed for use in PCR reactions to amplify all or part of the CRISPR locus. By "primer" is intended an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, and the use of the method.

PCR primers are preferably at least about 10 nucleotides in length, and most preferably at least about 20 nucleotides in length.

Compositions of the invention include oligonucleotide primers that may be used to amplify these repetitive regions. Examples of PCR primers that may be used in the methods of the invention include primers that bind to a region of genomic DNA flanking the CRISPR region, such as those found in SEQ ID NOS:49 and 50, or a primer that binds to SEQ ID NO:36, or primers that bind within the CRISPR region, or a combination thereof. The forward and reverse primers are designed to amplify all or part of a CRISPR region. By "flanking" is intended a region 5' (upstream) or 3' (downstream) of the sequence. In some embodiments, at least one primer binds to a DNA sequence flanking the CRISPR region. In some embodiments, one primer binds to the first repetitive sequence (for example, SEQ ID NO:2) and one primer binds to a flanking DNA sequence (for example, SEQ ID NO:36), therefore amplifying the entire CRISPR region. In some embodiments, both primers bind to regions of DNA flanking the CRISPR region. Primers that are designed to bind to DNA flanking a CRISPR region would be species specific, as this flanking DNA would not be expected to share enough sequence identity between all *Lactobacillus* species.

The repetitive sequences in these CRISPR regions show nucleotide homology to each other (see FIG. 7). The *L. acidophilus* repetitive sequences are at least 86% identical to each other. The *L. brevis* repetitive sequences are at least 82% identical to each other. The *L. delbrueckii* ssp. *bulgaricus* repetitive sequences are at least 89% identical to each other. The *L. acidophilus* repetitive sequences are at least 57% identical to the *L. brevis* repetitive sequences. The *L. acidophilus* repetitive sequences are at least 71% identical to the *L. casei* repetitive sequences. The *L. acidophilus* repetitive sequences are at least 75% identical to the *L. delbrueckii* repetitive sequences. The *L. brevis* repetitive sequences are at least 64% identical to the *L. casei* repetitive sequences. The *L. brevis* repetitive sequences are at least 64% identical to the *L. delbrueckii* repetitive sequences. The *L. casei* repetitive sequences are at least 71% identical to the *L. delbrueckii* repetitive sequences.

When the DNA sequence flanking the CRISPR region is known, one of skill in the art would be able to design primers for amplifying the CRISPR region based on this known flanking sequence. When the DNA sequence flanking the CRISPR region is not yet known, one of skill in the art would be able to determine this flanking sequence using methods known in the art. The entire genome of *L. acidophilus* NCFM is provided in U.S. Provisional Application No. 60/622,712, and Altermann et al. (2005) *Proc. Natl. Acad. Sci. U.S.A.* 102: 3906-3912, herein incorporated by reference in their entirety. The genome of *L. plantarum* is provided in Kleerebezem et al. (2003) *Proc. Natl. Acad. Sci. U.S.A.* 100:1990-1995. The entire genome of *L. johnsonii* is provided in Pridmore et al. (2004) *Proc. Natl. Acad. Sci. U.S.A* 101:2512-2517.

Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially mismatched primers, and the like.

With PCR, it is possible to amplify a single copy of a specific target sequence to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

Amplification in PCR requires "PCR reagents" or "PCR materials," which herein are defined as all reagents necessary to carry out amplification except the polymerase, primers, and template. PCR reagents normally include nucleic acid precursors (dCTP, dTTP, etc.), and buffer.

Once the DNA comprising the CRISPR locus or a portion thereof has been amplified, it may then be digested (cut) with a restriction enzyme. As used herein, the terms "restriction endonucleases" and "restriction enzymes" refer to bacterial enzymes, each of which cut double-stranded DNA at or near a specific nucleotide sequence. Restriction enzymes are well known in the art and may be readily obtained, for example, from variety of commercial sources (for example, New England Biolabs, Inc., Beverly, Mass.). Similarly, methods for using restriction enzymes are also generally well known and routine in the art. Preferred restriction enzymes are those that produce between 10 and 24 fragments of DNA when cutting the CRISPR locus (for example, SEQ ID NO:1). Examples of such enzymes include, but are not limited to, AluI, MseI, and Tsp5091. Fragments of DNA obtained using restriction enzymes may be detected, for example, as bands by gel electrophoresis. Restriction enzymes may be used to create Restriction Fragment Length Polymorphisms (RFLPs). RFLPs are, in essence, unique fingerprint snapshots of a piece of DNA, whether a whole chromosome (genome), or a part thereof, such as the region of the genome comprising the novel *L. acidophilus* CRISPR locus disclosed in the present invention.

RFLPs are generated by cutting ("restricting") a DNA molecule with a restriction endonuclease. Many hundreds of such enzymes have been isolated, as naturally made by bacteria. In essence, bacteria use such enzymes as a defensive system, to recognize and then cleave (restrict) any foreign DNA molecules that might enter the bacterial cell (e.g., a viral infection). Each of the many hundreds of different restriction enzymes has been found to cut (i.e., "cleave" or "restrict") DNA at a different sequence of the 4 basic nucleotides (A, T, G, C) that make up all DNA molecules, e.g., one enzyme might specifically and only recognize the sequence A-A-T-G-A-C, while another might specifically and only recognize the sequence G-T-A-C-T-A, etc. Depending on the unique enzyme involved, such recognition sequences may vary in length, from as few as 4 nucleotides to as many as 21 nucleotides. The larger the recognition sequence, the fewer restriction fragments will result, as the larger the recognition site, the lower the probability that it will repeatedly be found throughout the DNA.

Following the digestion, the resultant individual fragments are separated from one another based on their size. Any method suitable for separating DNA is encompassed by the methods of the present invention, including, but not limited to, gel electrophoresis, high performance liquid chromatography (HPLC), mass spectroscopy, and use of a microfluidic device. In one embodiment, the DNA fragments are separated by agarose gel electrophoresis. Gel electrophoresis separates different sized charged molecules by their rate of movement through a stationary gel under the influence of an electric current. These separated DNA fragments can easily be visualized, for example, by staining with ethidium bromide and by viewing the gel under UV illumination. The banding pattern reflects the sizes of the restriction digested DNA.

Alternatively to performing RFLP on the amplified CRISPR locus, the sequence of the amplified DNA may be obtained by any method known in the art, including automatic and manual sequencing methods. See, for example, Sambrook et al. (1989) *Molecular Cloning: A Laboratory Manual* (2d ed., Cold Spring Harbor Laboratory Press, Plainview, N.Y.; Roe et al. (1996) *DNA Isolation and Sequencing* (Essential Techniques Series, John Wiley & Sons).

Other methods that utilize the novel CRISPR repetitive regions of the invention to detect and/or type *Lactobacillus* strains are also encompassed by the invention. These methods include hybridization methods, either using a nucleic acid molecule of the invention as a probe, or a nucleic acid molecule capable of hybridizing to a disclosed nucleotide sequence of the present invention. See, for example, Sambrook et al. (1989) *Molecular Cloning: Laboratory Manual* (2d ed., Cold Spring Harbor Laboratory Press, Plainview, N.Y.).

In hybridization techniques, the hybridization probe(s) may be genomic DNA fragments, PCR-amplified products, or other oligonucleotides, and may comprise all or part of a known nucleotide sequence disclosed herein. In addition, it may be labeled with a detectable group such as $^{32}P$, or any other detectable marker, such as other radioisotopes, a fluorescent compound, an enzyme, or an enzyme co-factor. The term "labeled," with regard to the probe, is intended to encompass direct labeling of the probe by coupling (i.e., physically linking) a detectable substance to the probe, as well as indirect labeling of the probe by reactivity with another reagent that is directly labeled. Examples of indirect labeling include end-labeling of a DNA probe with biotin such that it can be detected with fluorescently labeled streptavidin.

Probes for hybridization can be made by labeling synthetic oligonucleotides based on the known CRISPR region nucleotide sequences disclosed herein. In one embodiment the entire *L. acidophilus* CRISPR region nucleotide sequence (SEQ ID NO:1) is used as a probe to detect and/or differentiate an *L. acidophilus* strain. In another embodiment, the probe is a fragment of a nucleotide sequence disclosed herein, such as a probe consisting of a single repetitive sequence, as found in any of SEQ ID NOS:2-7 and 37-48. In yet another embodiment, the probe is a sequence found in a spacer region, for example in any of SEQ ID NOS:8-35. In another embodiment, the probe is a flanking region, such as that of SEQ ID NO:36. The hybridization probe typically comprises a region of nucleotide sequence that hybridizes under stringent conditions to at least about 10, preferably about 20, more preferably about 50, 75, 100, 125, 150, 175, 200, 250, 300, 350, or 400 consecutive nucleotides of a CRISPR region nucleotide sequence of the invention or a fragment or variant thereof. Preparation of probes for hybridization is generally known in the art and is disclosed in Sambrook et al. (1989) *Molecular Cloning: A Laboratory Manual* (2d ed., Cold Spring Harbor Laboratory Press, Plainview, N.Y.), herein incorporated by reference.

Substantially identical sequences will hybridize to each other under stringent conditions. By "stringent conditions" is intended conditions under which a probe will hybridize to its target sequence to a detectably greater degree than to other sequences (e.g., at least 2-fold over background). Stringent conditions are known in the art and can be found in *Current Protocols in Molecular Biology* (John Wiley & Sons, New York (1989)), 6.3.1-6.3.6.

When using probes, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides).

The post-hybridization washes are instrumental in controlling specificity. The two critical factors are ionic strength and temperature of the final wash solution. For the detection of sequences that hybridize to a full-length or approximately full-length target sequence, the temperature under stringent conditions is selected to be about 5° C. lower than the thermal melting point ($T_m$) for the specific sequence at a defined ionic strength and pH. However, stringent conditions would encompass temperatures in the range of 1° C. to 20° C. lower than the $T_m$, depending on the desired degree of stringency as otherwise qualified herein. For DNA-DNA hybrids, the $T_m$ can be determined using the equation of Meinkoth and Wahl (1984) *Anal. Biochem.* 138:267-284: $T_m$=81.5° C.+16.6 (logM)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe.

The ability to detect sequences with varying degrees of homology can be obtained by varying the stringency of the hybridization and/or washing conditions. To target sequences that are 100% identical (homologous probing), stringency conditions must be obtained that do not allow mismatching. By allowing mismatching of nucleotide residues to occur, sequences with a lower degree of similarity can be detected (heterologous probing). For every 1% of mismatching, the $T_m$ is reduced about 1° C.; therefore, hybridization and/or wash conditions can be manipulated to allow hybridization of sequences of a target percentage identity. For example, if sequences with ≧90% sequence identity are preferred, the $T_m$ can be decreased by 10° C.

Exemplary low stringency conditions include hybridization with a buffer solution of 30-35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Methods that encompass hybridization techniques to detect or differentiate bacterial strains are also encompassed. These include, but are not limited to, Southern blotting (see, for example, Van Embden et al. (1993) *J. Clin. Microbiol.* 31:406-409), shift mobility assays (see, for example, U.S. Published Application No. 20030219778), sequencing assays using oligonucleotide arrays (see, for example, Pease et al. (1994) *Proc. Natl. Acad. Sci. USA* 91:5022-5026), spoligotyping (see, for example, Kamerbeek et al. (1997) *J. Clin. Microbiol.* 35:907-914), Flourescent In Situ Hybridization (FISH) (see, for example, Amann et al. (1990) *J. Bacteria* 172:762-770) and heteroduplex tracking assays or heteroduplex mobility analysis (see, for example, White et al. (2000) *J. Clin. Micro.* 38:477-482).

The invention also encompasses kits for detecting the presence of the nucleic acids of the present invention in a sample. Such kits can be used for typing or detection of *Lactobacillus* strains present in, for example, a food product or starter culture, or in a subject that has consumed a probiotic material. For example, the kit may comprise PCR primers for amplification of a CRISPR locus, as well as a polymerase and other PCR materials for use in DNA amplification. The kit may also contain one or more restriction enzymes for use in RFLP analysis. The kit may contain a labeled compound or agent capable of detecting a disclosed nucleic acid sequence in a sample and means for determining the amount of a the disclosed nucleic acid sequence in the sample (e.g., an oligonucleotide probe that binds to a nucleic acid sequence of the invention, e.g., any of SEQ ID NOS:1-50).

For oligonucleotide-based kits, the kit may comprise, for example: (1) an oligonucleotide, e.g., a detectably labeled oligonucleotide, that hybridizes to a disclosed nucleic acid sequence, or (2) a pair of primers useful for amplifying a disclosed nucleic acid molecule.

The kit may also comprise, e.g., a buffering agent, a preservative, or a protein-stabilizing agent. The kit may also comprise components necessary for detecting the detectable agent (e.g., an enzyme or a substrate). The kit may also contain a control sample or a series of control samples (both positive and negative) that can be assayed and compared to the test sample contained. Each component of the kit is usually enclosed within an individual container, and all of the various containers are within a single package along with instructions for use.

In one embodiment, the kit comprises multiple probes in an array format, such as those described, for example, in U.S. Pat. Nos. 5,412,087 and 5,545,531, and International Publication No. WO 95/00530, herein incorporated by reference. Probes for use in the array may be synthesized either directly onto the surface of the array, as disclosed in International Publication No. WO 95/00530, or prior to immobilization onto the array surface (Gait, ed. (1984) *Oligonucleotide Synthesis a Practical Approach* (IRL Press, Oxford, England). The probes may be immobilized onto the surface using techniques well known to one of skill in the art, such as those described in U.S. Pat. No. 5,412,087. Probes may be a nucleic acid or peptide sequence, preferably purified.

The arrays may be used to screen organisms, samples, or products to differentiate between *Lactobacillus* strains, or to verify the presence of a *Lactobacillus* species, such as *L. acidophilus* NCFM®. Binding to a capture probe is detected, for example, by signal generated from a label attached to the nucleic acid molecule comprising the disclosed nucleic acid sequence. The method can include contacting the molecule comprising the disclosed nucleic acid with a first array having a plurality of capture probes and a second array having a different plurality of capture probes. The results of each hybridization can be compared to analyze differences in the content between a first and second sample. The first plurality of capture probes can be from a control sample, e.g., a sample known to contain *L. acidophilus* NCFM®, or control subject, e.g., a food, including an animal feed or animal feed supplement, a dietary supplement, a starter culture sample, or a biological fluid. The second plurality of capture probes can be from an experimental sample, e.g., a subject that has consumed a probiotic material, a starter culture sample, a food, or a biological fluid.

These assays may be especially useful in microbial selection and quality control procedures where the detection of unwanted materials is essential. The detection of particular nucleotide sequences may also be useful in determining the genetic composition of food, fermentation products, or industrial microbes, or microbes present in the digestive system of animals or humans that have consumed probiotics.

Fragments and Variants

The invention includes isolated nucleic acid molecules comprising the nucleotide sequence of a CRISPR locus from *L. acidophilus, L. brevis, L. casei, L. delbrueckii*, or variants and fragments thereof. By "fragment" of a nucleic acid molecule is intended a portion of the nucleotide sequence. Fragments of nucleic acid molecules can be used as hybridization probes to detect and/or differentiate CRISPR regions from various bacteria, including *Lactobacillus* species, or can be used as primers in PCR amplification of CRISPR regions. Fragments of nucleic acids can also be bound to a physical substrate to comprise what may be considered a macro- or microarray (for example, U.S. Pat. Nos. 5,837,832 and 5,861,242). Such arrays of nucleic acids may be used to identify nucleic acid molecules with sufficient identity to the target sequences. By "nucleic acid molecule" is intended DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. A nucleotide fragment may be used as a hybridization probe or PCR primer as described above. Fragments of CRISPR region nucleic acid molecules comprise at least about 15, 20, 50, 75, 100, 200, 250, 300, 350, 400, 450, 500, 550, 600, 650, 700, 750, 800, 850, 900, 950, 1000, 1100, 1200, 1300, 1400, 1500, 1600, 1700, 1800, 1900 nucleotides or up to the total number of nucleotides present in a full-length CRISPR region nucleotide sequence as disclosed herein (for example, 1953 for SEQ ID NO:1).

Variants of the nucleotide sequences are encompassed in the present invention. By "variant" is intended a sufficiently identical sequence. Accordingly, the invention encompasses isolated nucleic acid molecules that are sufficiently identical to any of the nucleotide sequences of SEQ ID NOS:1-50, or nucleic acid molecules that hybridize to any of the nucleotide sequences of SEQ ID NOS:1-50, or a complement thereof, under stringent conditions.

In general, nucleotide sequences that have at least about 45%, 55%, or 65% identity, preferably at least about 70% or 75% identity, more preferably at least about 78%, 80%, 81%, 82%, 83%, 84%, 85%, 86%, 87%, 88%, 89%, or 90%, most preferably at least about 91%, 92%, 93%, 94%, 95%, 96%, 97%, 98%, or 99% sequence identity to any of the nucleotide sequences of SEQ ID NOS:1-50, are defined herein as sufficiently identical.

Naturally occurring variants may exist within a population (e.g., the *L. acidophilus* population). Such variants can be identified by using well-known molecular biology techniques, such as PCR, and hybridization as described above. Synthetically derived nucleotide sequences, for example, sequences generated by site-directed mutagenesis or PCR-mediated mutagenesis, that still allow strain differentiation or detection, are also included as variants. One or more nucleotide substitutions, additions, or deletions can be introduced into a nucleotide sequence disclosed herein, such that the substitutions, additions, or deletions do not affect the ability to differentiate strains based on any of the methods disclosed herein or known in the art, including, but not limited to RFLP, sequencing, and hybridization. Examples of variants of a CRISPR repeat region can be found in SEQ ID NOS:2-7 and 37-48.

Sequence Identity

The nucleotide sequences encompassed by the present invention have a certain sequence identity. By "sequence identity" is intended the nucleotide residues that are the same when aligning two sequences for maximum correspondence over a specified comparison window. By "comparison window" is intended a contiguous segment of the two nucleotide sequences for optimal alignment, wherein the second sequence may contain additions or deletions (i.e., gaps) as compared to the first sequence. Generally, for nucleic acid alignments, the comparison window is at least 20 contiguous nucleotides in length, and optionally can be 30, 40, 50, 100, or longer. Those of skill in the art understand that to avoid a high similarity due to inclusion of gaps, a gap penalty is typically introduced and is subtracted from the number of matches.

To determine the percent identity of two nucleotide sequences, an alignment is performed. Percent identity of the two sequences is a function of the number of identical residues shared by the two sequences in the comparison window (i.e., percent identity=number of identical residues/total number of residues×100). In one embodiment, the sequences are the same length. Methods similar to those mentioned below can be used to determine the percent identity between two sequences. The methods can be used with or without allowing gaps.

Mathematical algorithms can be used to determine the percent identity of two sequences. Non-limiting examples of mathematical algorithms are the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877; the algorithm of Myers and Miller (1988) *CABIOS* 4:11-17; the local homology algorithm of Smith et al. (1981) *Adv. Appl. Math.* 2:482; the global alignment algorithm of Needleman and Wunsch (1970) *J. Mol. Biol.* 48:443-453; and the search-for-local alignment-method of Pearson and Lipman (1988) *Proc. Natl. Acad. Sci. USA* 85:2444-2448.

Various computer implementations based on these mathematical algorithms have been designed to enable the determination of sequence identity. The BLAST programs of Altschul et al. (1990) *J. Mol. Biol.* 215:403 are based on the algorithm of Karlin and Altschul (1990) supra. Searches to obtain nucleotide sequences that are homologous to nucleotide sequences of the present invention can be performed with the BLASTN program, score=100, wordlength=12. Gapped alignments may be obtained by using Gapped BLAST (in BLAST 2.0) as described in Altschul et al. (1997) *Nucleic Acids Res.* 25:3389. To detect distant relationships between molecules, PSI-BLAST can be used. See, Altschul et al. (1997) supra. For all of the BLAST programs, the default parameters of the respective programs can be used. See, www.ncbi.nlm.nih.gov. Alignment may also be performed manually by inspection.

Another program that can be used to determine percent sequence identity is the ALIGN program (version 2.0), which uses the mathematical algorithm of Myers and Miller (1988) supra. In addition to the ALIGN and BLAST programs, the BESTFIT, GAP, FASTA and TFASTA programs are part of the GCG Wisconsin Genetics Software Package, Version 10 (available from Accelrys Inc., 9685 Scranton Rd., San Diego, Calif., USA), and can be used for performing sequence alignments. The preferred program is GAP version 10, which used the algorithm of Needleman and Wunsch (1970) supra. Unless otherwise stated the sequence identity values provided herein refer to those values obtained by using GAP Version 10 with the following parameters: % identity using GAP Weight of 50 and Length Weight of 3 and the nwsgapdna.cmp scoring matrix. Other equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The following examples are offered by way of illustration and not by way of limitation.

EXPERIMENTAL

Example 1

DNA Analysis

The genomic DNA sequence from *Lactobacillus acidophilus* NCFM® was analyzed for repetitive DNA by a "repeat and match analysis" using Applied Maths' Kodon software package. One intergenic region between DNA polymerase I (polA) (ORF 1550) and a putative phosphoribosylamine-glycine ligase (purD) (ORF 1551) was identified as having features characteristic of a CRISPR locus. This region is approximately 2.4 kb long and contains 32 nearly perfect repeats of 29 base pairs separated by 32 base pair spacers (see FIGS. 1 and 2).

A number of features of the CRISPR region can be seen in FIG. 2. The 29 base pair repeats are highlighted. The first nucleotide of the repeat is either an A or a G. The last nucleotide of the repeat changes from a T to a C at repeat number 21. An imperfect inverted repeat is indicated by an underline on the last repeat. The first repeat contains two A→T base substitutions. The $26^{th}$ repeat contains one C→T base substitution. Two sequences are repeated in the spacer region; one is repeated twice (bolded and outlined) and one is repeated three times (bolded and caps). The $16^{th}$ spacer region is one base longer than the others.

Example 2

PCR of Intergenic Region

Primers were designed to amplify the entire intergenic region between polA and purD (expected product size=2582 base pairs). The primers were as follows:

```
                                         (SEQ ID NO: 49)
1550_F-5' GCA TTA GTG TGC AAC CCA TCT GG 3'

(SEQ ID NO: 50)
1551_R-5' GAT CTG CTG GAT TGC TTC TAC CG 3'
```

A PCR reaction mix was set up for each reaction (25.0 µl of AccuPrime SuperMix II (2× conc.); 1.0 µl of each primer (20 µM); 1 µl of template (300 ng/µl); H$_2$O to 50.0 µl). The reaction conditions were as follows: 1 cycle at 95° C. for 5 minutes; 40 cycles with a first step at 95° C. for 30 seconds, a second step at 54° C. for 30 seconds, and a third step at 68° C. for 3 minutes; 1 cycle at 68° C. for 7 minutes.

This PCR was performed on sixteen *L. acidophilus* strains. All *L. acidophilus* strains that had previously been shown to be identical to *L. acidophilus* NCFM® by other means (i.e., PFGE, Microarrays, 16S sequencing, etc.) generated the same size PCR amplicon. Three strains that had previously been shown to be different from NCFM® (ATCC 4356, ATCC 4357, and Strain B) exhibited different sized amplicons. Strains of *Lactobacillus helveticus, Lactobacillus gasseri*, and *Lactobacillus plantarum* that were tested did not generate a PCR product.

Four strains were found that did not generate a PCR product: *L. acidophilus* ATCC 521, *L. acidophilus* strain F, *L. acidophilus* strain G, and *L. acidophilus* strain H. These strains were sent to MIDI Labs for identification and were identified as follows:

| | |
|---|---|
| *L. acidophilus* ATCC 521 | *L. helveticus* |
| *L. acidophilus* strain F | *Pediococcus parvules* |
| *L. acidophilus* strain G | *L. gasseri* |
| *L. acidophilus* strain H | *L. plantarum* |

The PCR results for 6 strains are shown in FIG. 3A. The different sized bands indicated that there were significant differences in the CRISPR region of some strains.

Example 3

PCR Amplification Method is Specific for *Lactobacillus acidophilus* Detection

Figure 4:
FIG. 4 is a micrograph of PCR products of the following strains: Lane 1—*L. acidophilus* NCFM®; Lane 2—*L. acidophilus* Lac-1; Lane 3—*L. acidophilus* Lac-2; Lane 4—*L. acidophilus* Lac-3; Lane 5—*L. acidophilus* ATCC 4355; Lane 6—*L. acidophilus* ATCC 4356; Lane 7—*L. acidophilus* ATCC 4357; Lane 8—*L. acidophilus* ATCC 4796; Lane 9—*L. helveticus* ATCC 521; Lane 10—*L. acidophilus* ATCC 832; Lane 11—*L. acidophilus* ATCC 9224; Lane 12—*L. acidophilus* ATCC 11975; Lane 13—*L. acidophilus* ATCC 314; Lane 14—*L. gasseri* ATCC 43121; Lane 15—*L. acidophilus* Lac-4; Lane 16—*L. acidophilus* Lac-5; Lane 17—*L. amylovorus* ATCC 33198; Lane 18—*L. gallinarum* ATCC 33199; Lane 19—*L. gasseri* ATCC 33323; Lane 20—*L. johnsonii* ATCC 33200; Lane 21—*L. crispatus* Lcr-1; Lane 22—*L. helveticus* Lhe-1; Lane 23—control (no DNA).

PCR was performed on 23 bacterial samples as described in Example 2. PCR amplification of all *L. acidophilus* strains tested resulted in a PCR amplicon, whereas all other species tested did not (see FIG. 4). The species of all tested strains were confirmed using 16S sequencing. Therefore, this method is specific for *L. acidophilus*.

Example 4

Restriction Digestion of Intergenic Region

In order to generate more discriminatory patterns for each strain, the CRISPR PCR products were subjected to restriction digestion with three enzymes that generated between 10 and 24 bands: AluI—10 bands; MseI—19 bands; Tsp509I—24 bands.

AluI: Six CRISPR PCR products were digested with AluI and separated on a 2% agarose gel (FIG. 3B). Three strains exhibited a difference in banding pattern, ATCC 4356, ATCC 4357, and strain B. These results are in agreement with the results of other tests (Microarray, Transposase-PCR, PFGE) that indicate these three strains are unique (data not shown).

MseI: Six CRISPR PCR products were digested with MseI and separated on a 3% agarose gel (FIG. 3C).

Tsp509I: Six CRISPR PCR products were digested with Tsp509I and separated on a 3% agarose gel (FIG. 3D).

Example 5

Figure 5:
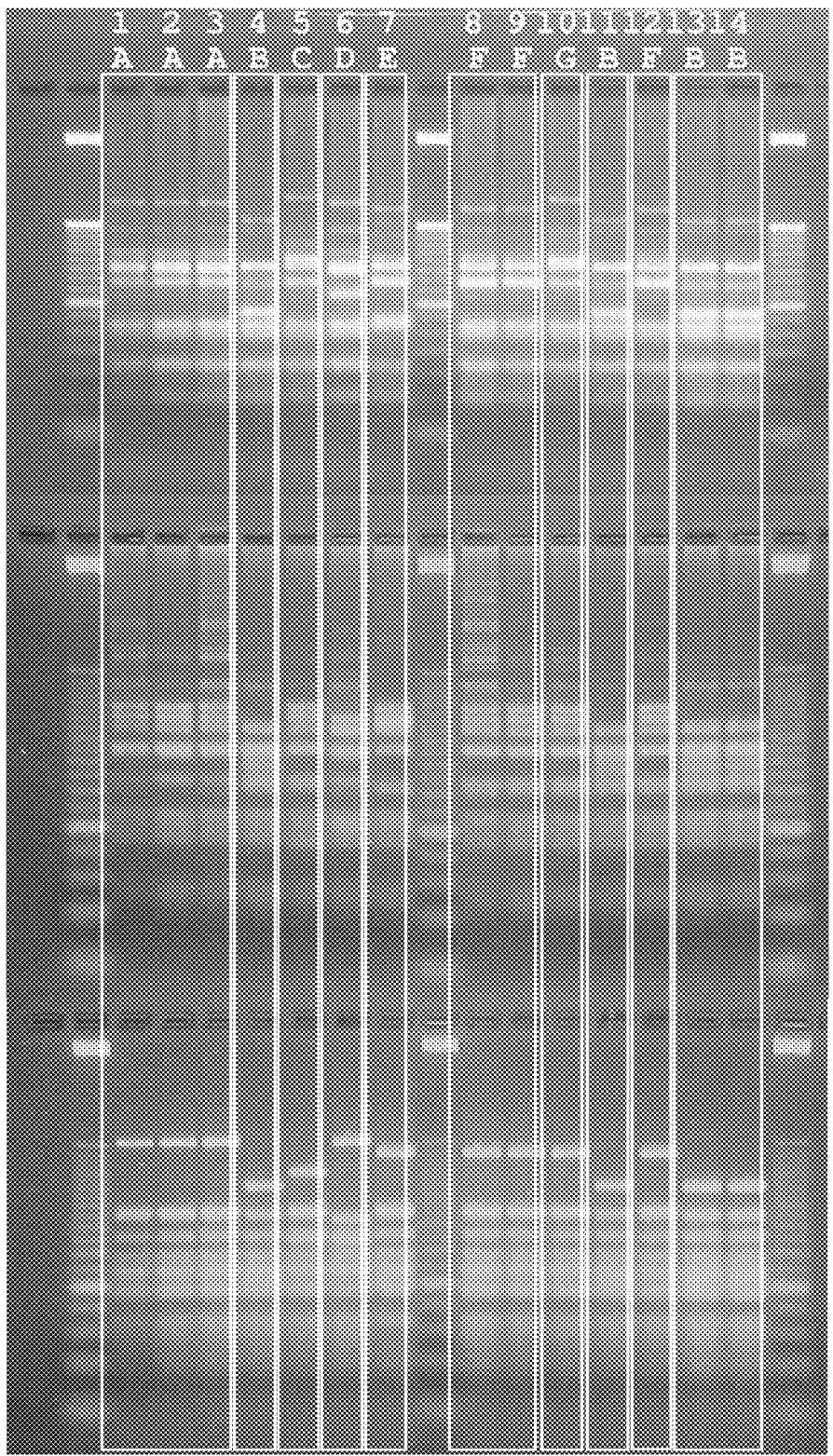
FIG. 5 is a micrograph of bands resulting from PCR amplification followed by restriction digest of the following strains: Lane 1—*L. acidophilus* NCFM®; Lane 2—*L. acidophilus* Lac-1; Lane 3—*L. acidophilus* Lac-2; Lane 4—*L. acidophilus* Lac-3; Lane 5—*L. acidophilus* ATCC 4355; Lane 6—*L. acidophilus* ATCC 4356; Lane 7—*L. acidophilus* ATCC 4357; Lane 8—*L. acidophilus* ATCC 4796; Lane 9—*L. acidophilus* ATCC 832; Lane 10—*L. acidophilus* ATCC 9224; Lane 11—*L. acidophilus* ATCC 11975; Lane 12—*L. acidophilus* ATCC 314; Lane 13—*L. acidophilus* Lac-4; Lane 14—*L. acidophilus* Lac-5.

PCR Amplification Followed by Enzymatic Digestion Can Differentiate *L. acidophilus* Strains Fourteen *L. acidophilus* strains were subjected to both CRISPR locus amplification and restriction enzyme digestion as described in Examples 2 and 4. Seven distinct band patterns were generated, indicating that this method can differentiate between strains (see FIG. 5).

Example 6

PCR/Digestion Products Match PFGE Results

Figure 6:
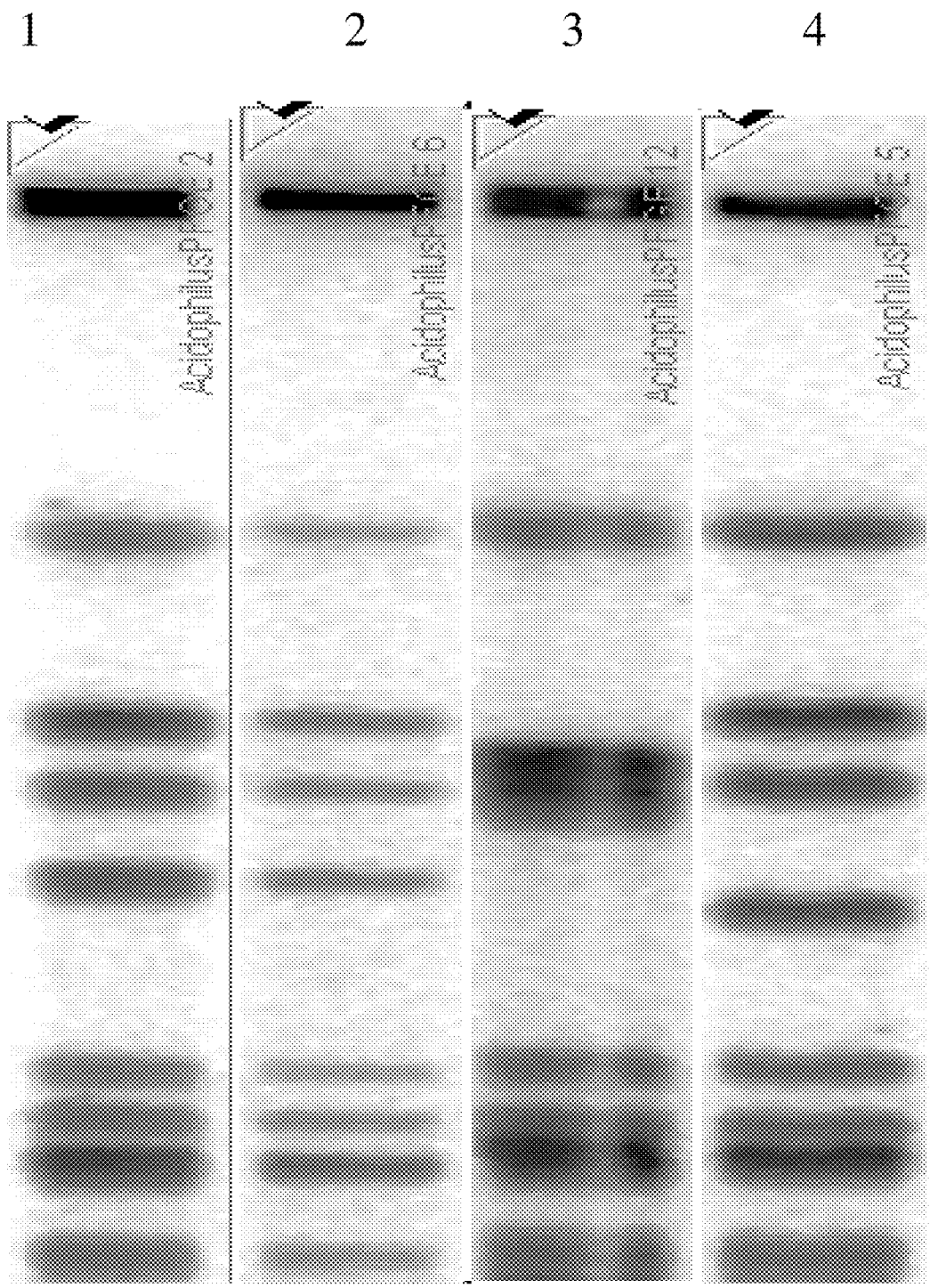
FIG. 6 is a micrograph showing pulsed field gel electrophoresis of *L. acidophilus* NCFM® (Lane 1); *L. acidophilus* Lac-1 (Lane 2); *L. acidophilus* Lac-3 (Lane 3); and *L. acidophilus* ATCC 4356 (Lane 4).

PFGE was performed on the fourteen *L. acidophilus* strains discussed in Example 5. The PFGE results confirmed those obtained by using the PCR/Digestion Method as described in Examples 2-5 (see FIG. 6). NCFM® and Lac-1 strains showed identical PFGE and PCR/Digestion results, but differed from Lac-3 and ATCC4356.

Example 7

Identification of CRISPR Regions on Other *Lactobacillus* Species

Other *Lactobacillus* species were analyzed for CRISPR sequences as described in Example 1. CRISPR sequences were found in *L. brevis, L. casei* and *L. delbrueckii* ssp. *bulgaricus*. The repeat sequences are shown in FIG. 7, with variant nucleotides shown below the main sequences. Within the regions analyzed, 32 repeats were present in *L. acidophilus*, 12 repeats were present in *L. brevis*, 21 repeats were present in *L. casei*, and 17 repeats were present in *L. delbrueckii* ssp. *bulgaricus*.

Example 8

Strain Typing of *Lactabacillus* Species

Primers are designed to amplify the entire CRISPR region of *L. delbrueckii* ssp. *bulgaricus*. A PCR reaction mixture is set up and PCR is performed on ten *L. delbrueckii* ssp. *bulgaricus* strains, as described in Example 2. The PCR products are subjected to restriction digestion with AluI, MseI, and Tsp509I as described in Example 4. The DNA is separated by gel electrophoresis and the band patterns are analyzed. Detection of different band patterns indicates the presence of different strains of *L. delbrueckii* ssp. *bulgaricus*.

CONCLUSIONS

The identification of a unique CRISPR region in NCFM® is a promising discovery for the development of detection and differentiation methods. Of 20 strains designated as *L. acidophilus* tested, 16 generated a CRISPR-PCR fragment with the designed primers. The four strains for which no fragment was amplified were confirmed by MIDI Labs as being misidentified—strengthening the position of this CRISPR locus as being *L. acidophilus* specific. The remaining 16 strains were subjected to restriction analysis of the CRISPR-PCR fragment revealing 12 strains with identical restriction patterns and 3 strains with unique patterns. These results are supported by data that has been generated independently by comparative genome microarray analysis, transposase-PCR analysis, and PFGE.

In summary, a relatively quick and easy CRISPR-PCR/restriction analysis generated unique fragmentation patterns for the truly different *L. acidophilus* strains tested. The method can also be applied in other *Lactobacillus* species, including *L. brevis, L. casei*, and *L. delbrueckii*.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for typing a *Lactobacillus* species having a Clustered Regularly Interspaced Short Palindromic Repeat (CRISPR) region, comprising:
   a) obtaining a sample comprising said *Lactobacillus*;
   b) amplifying a region of DNA comprising said CRISPR region or a fragment thereof in said sample to create amplified DNA, ; and
   c) typing a *Lactobacillus* species having a Clustered Regularly Interspaced Short Palindromic Repeat (CRISPR) region.

2. The method of claim 1 comprising the further steps;
   c) adding to said amplified DNA at least one restriction enzyme that recognizes one or more sites in said amplified DNA;
   d) incubating said restriction enzyme with said amplified DNA for a time sufficient to form restriction fragments;
   e) determining the number of said restriction fragments and their size; and,
   f) typing said bacterium based on said number and size of said restriction fragments.

3. The method of claim 1, further comprising the step of sequencing said amplified DNA.

4. A method for typing a *Lactobacillus* species having a Clustered Regularly Interspaced Short Palindromic Repeat (CRISPR) region, comprising:
   a) obtaining a sample comprising said *Lactobacillus*;
   b) amplifying a region of DNA comprising said CRISPR region or a fragment thereof in said sample to create amplified DNA, the CRISPR region including at least one CRISPR repeat region or CRISPR spacer region or a portion thereof; and
   c) typing a *Lactobacillus* species having a Clustered Regularly Interspaced Short Palindromic Repeat (CRISPR) region.

5. The method of claim 4 comprising the further steps;
   c) adding to said amplified DNA at least one restriction enzyme that recognizes one or more sites in said amplified DNA;
   d) incubating said restriction enzyme with said amplified DNA for a time sufficient to form restriction fragments;
   e) determining the number of said restriction fragments and their size; and,
   f) typing said bacterium based on said number and size of said restriction fragments.

6. The method of claim 4, further comprising the step of sequencing said amplified DNA.

7. The method of claim 4, wherein amplifying a region of DNA includes providing a first primer that binds to a repetitive sequence in a CRISPR region.

8. The method of claim 7, wherein amplifying a region of DNA includes providing a second primer that binds to DNA flanking the CRISPR region.

* * * * *